(12) United States Patent
Song et al.

(10) Patent No.: US 7,670,786 B2
(45) Date of Patent: *Mar. 2, 2010

(54) MEMBRANE-BASED ASSAY DEVICES

(75) Inventors: Xuedong Song, Roswell, GA (US); Rosann Marie Matthews Kaylor, Cumming, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/876,018

(22) Filed: Oct. 22, 2007

(65) Prior Publication Data

US 2008/0096288 A1 Apr. 24, 2008

Related U.S. Application Data

(62) Division of application No. 10/228,836, filed on Aug. 27, 2002, now Pat. No. 7,285,424.

(51) Int. Cl.
G01N 33/53 (2006.01)
(52) U.S. Cl. .................. 435/7.1; 435/7.2; 435/7.21; 435/7.32; 435/239; 435/803; 435/805; 435/970; 436/514; 436/518; 436/531; 436/536; 436/533; 436/538; 436/806; 436/824
(58) Field of Classification Search .................. 435/7.1, 435/7.02, 7.21, 7.32, 239, 803, 805, 970; 436/514, 518, 531, 536, 533, 538, 806, 824
See application file for complete search history.

(56) References Cited

U.S. PATENT DOCUMENTS

| | | | |
|---|---|---|---|
| 1,366,241 A | 1/1921 | Burch | |
| 3,700,623 A | 10/1972 | Keim | |
| 3,772,076 A | 11/1973 | Keim | |
| 4,094,647 A | 6/1978 | Deutsch et al. | |
| 4,110,529 A | 8/1978 | Stoy | |
| 4,168,146 A | 9/1979 | Grubb et al. | |
| RE30,267 E | 5/1980 | Bruschi | |
| 4,210,723 A | 7/1980 | Dorman et al. | |
| 4,235,601 A | 11/1980 | Deutsch et al. | |
| 4,275,149 A | 6/1981 | Litman et al. | |
| 4,312,228 A | 1/1982 | Wohltjen | |
| 4,361,537 A | 11/1982 | Deutsch et al. | |
| 4,363,874 A | 12/1982 | Greenquist | |
| 4,366,241 A | 12/1982 | Tom et al. | |
| 4,374,925 A | 2/1983 | Litman et al. | |
| 4,385,126 A | 5/1983 | Chen et al. | |
| 4,426,451 A | 1/1984 | Columbus | |
| 4,427,836 A | 1/1984 | Kowalski et al. | |
| 4,435,504 A | 3/1984 | Zuk et al. | |
| 4,441,373 A | 4/1984 | White | |
| 4,442,204 A | 4/1984 | Greenquist et al. | |
| 4,444,592 A | 4/1984 | Ludwig | |
| 4,477,635 A | 10/1984 | Mitra | |
| 4,480,042 A | 10/1984 | Craig et al. | |
| 4,533,499 A | 8/1985 | Clark et al. | |
| 4,533,629 A | 8/1985 | Litman et al. | |
| 4,534,356 A | 8/1985 | Papadakis | |
| 4,537,657 A | 8/1985 | Keim | |
| 4,537,861 A | 8/1985 | Elings et al. | |
| 4,540,659 A | 9/1985 | Litman et al. | |
| 4,552,458 A | 11/1985 | Lowne | |
| 4,561,286 A | 12/1985 | Sekler et al. | |
| 4,562,157 A | 12/1985 | Lowe et al. | |
| 4,586,695 A | 5/1986 | Miller | |
| 4,595,661 A | 6/1986 | Cragle et al. | |
| 4,596,697 A | 6/1986 | Ballato | |
| 4,614,723 A | 9/1986 | Schmidt et al. | |
| 4,632,559 A | 12/1986 | Brunsting | |
| 4,661,235 A | 4/1987 | Krull et al. | |
| 4,698,262 A | 10/1987 | Schwartz et al. | |
| 4,703,017 A | 10/1987 | Campbell et al. | |
| 4,722,889 A | 2/1988 | Lee et al. | |
| 4,727,019 A | 2/1988 | Valkirs et al. | |
| 4,731,337 A | 3/1988 | Luotola et al. | |

(Continued)

FOREIGN PATENT DOCUMENTS

EP 0073593 A1 3/1983

(Continued)

OTHER PUBLICATIONS

8 Photographs of Accu-chek® Blood Glucose Meter.

(Continued)

*Primary Examiner*—Bao-Thuy L Nguyen
(74) *Attorney, Agent, or Firm*—Dority & Manning, P.A.

(57) ABSTRACT

A membrane-based assay device for detecting the presence or quantity of an analyte residing in a test sample is provided. The device utilizes a self-calibrated magnetic binding assay format (e.g., sandwich, competitive, etc.) that includes detection probes capable of generating a detection signal (e.g., fluorescent non-magnetic particles) and calibration probes capable of generating a calibration signal (e.g., fluorescent magnetic particles). The amount of the analyte within the test sample is proportional (e.g., directly or inversely) to the intensity of the detection signal calibrated by the intensity of the calibration signal. It has been discovered that the fluidics-based device of the present invention provides an accurate, inexpensive, and readily controllable method of determining the presence of an analyte in a test sample.

10 Claims, 7 Drawing Sheets

U.S. PATENT DOCUMENTS

| | | |
|---|---|---|
| 4,742,011 A | 5/1988 | Blake et al. |
| 4,743,542 A | 5/1988 | Graham, Jr. et al. |
| 4,743,560 A | 5/1988 | Campbell et al. |
| 4,776,944 A | 10/1988 | Janata et al. |
| 4,835,099 A | 5/1989 | Mize et al. |
| 4,837,168 A | 6/1989 | de Jaeger et al. |
| 4,842,783 A | 6/1989 | Blaylock |
| 4,843,000 A | 6/1989 | Litman et al. |
| 4,843,021 A | 6/1989 | Noguchi et al. |
| 4,844,613 A | 7/1989 | Batchelder et al. |
| 4,849,338 A | 7/1989 | Litman et al. |
| 4,855,240 A | 8/1989 | Rosenstein et al. |
| 4,857,453 A | 8/1989 | Ullman et al. |
| 4,877,586 A | 10/1989 | Devaney, Jr. et al. |
| 4,877,747 A | 10/1989 | Stewart |
| 4,889,816 A | 12/1989 | Davis et al. |
| 4,895,017 A | 1/1990 | Pyke et al. |
| 4,904,583 A | 2/1990 | Mapes et al. |
| 4,916,056 A | 4/1990 | Brown, III et al. |
| 4,917,503 A | 4/1990 | Bhattacharjee |
| 4,920,046 A | 4/1990 | McFarland et al. |
| 4,940,734 A | 7/1990 | Ley et al. |
| 4,954,435 A | 9/1990 | Krauth |
| 4,956,302 A | 9/1990 | Gordon et al. |
| 4,963,498 A | 10/1990 | Hillman et al. |
| 4,973,670 A | 11/1990 | McDonald et al. |
| 4,978,625 A | 12/1990 | Wagner et al. |
| 4,980,298 A | 12/1990 | Blake et al. |
| 4,992,385 A | 2/1991 | Godfrey |
| 5,003,178 A | 3/1991 | Livesay |
| 5,023,053 A | 6/1991 | Finlan |
| 5,026,653 A | 6/1991 | Lee et al. |
| 5,035,863 A | 7/1991 | Finlan et al. |
| 5,055,265 A | 10/1991 | Finlan |
| 5,063,081 A | 11/1991 | Cozzette et al. |
| 5,064,619 A | 11/1991 | Finlan |
| 5,073,340 A | 12/1991 | Covington et al. |
| 5,075,077 A | 12/1991 | Durley, III et al. |
| 5,075,078 A | 12/1991 | Osikowicz et al. |
| 5,076,094 A | 12/1991 | Frye et al. |
| 5,096,671 A | 3/1992 | Kane et al. |
| 5,114,676 A | 5/1992 | Leiner et al. |
| 5,120,643 A | 6/1992 | Ching et al. |
| 5,120,662 A | 6/1992 | Chan et al. |
| 5,124,254 A | 6/1992 | Hewlins et al. |
| 5,134,057 A | 7/1992 | Kuypers et al. |
| 5,137,609 A | 8/1992 | Manian et al. |
| 5,143,854 A | 9/1992 | Pirrung et al. |
| 5,145,784 A | 9/1992 | Cox et al. |
| 5,149,622 A | 9/1992 | Brown et al. |
| 5,152,758 A | 10/1992 | Kaetsu et al. |
| 5,156,953 A | 10/1992 | Litman et al. |
| 5,182,135 A | 1/1993 | Giesecke et al. |
| 5,185,127 A | 2/1993 | Vonk |
| 5,196,350 A | 3/1993 | Backman et al. |
| 5,200,084 A | 4/1993 | Liberti et al. |
| 5,208,143 A | 5/1993 | Henderson et al. |
| 5,208,535 A | 5/1993 | Nakayama et al. |
| 5,221,454 A | 6/1993 | Manian et al. |
| 5,225,935 A | 7/1993 | Watanabe et al. |
| 5,234,813 A | 8/1993 | McGeehan et al. |
| 5,235,238 A | 8/1993 | Nomura et al. |
| 5,238,815 A | 8/1993 | Higo et al. |
| 5,242,828 A | 9/1993 | Bergström et al. |
| 5,252,459 A | 10/1993 | Tarcha et al. |
| 5,262,299 A | 11/1993 | Evangelista et al. |
| 5,268,306 A | 12/1993 | Berger et al. |
| 5,275,785 A | 1/1994 | May et al. |
| 5,314,923 A | 5/1994 | Cooke et al. |
| 5,316,727 A | 5/1994 | Suzuki et al. |
| 5,320,944 A | 6/1994 | Okada et al. |
| 5,321,492 A | 6/1994 | Detwiler et al. |
| 5,327,225 A | 7/1994 | Bender et al. |
| 5,330,898 A | 7/1994 | Bar-Or et al. |
| 5,342,759 A | 8/1994 | Litman et al. |
| 5,352,582 A | 10/1994 | Lichtenwalter et al. |
| 5,356,782 A | 10/1994 | Moorman et al. |
| 5,358,852 A | 10/1994 | Wu |
| 5,369,717 A | 11/1994 | Attridge |
| 5,374,563 A | 12/1994 | Maule |
| 5,376,255 A | 12/1994 | Gumbrecht et al. |
| 5,387,503 A | 2/1995 | Selmer et al. |
| 5,395,754 A | 3/1995 | Lambotte et al. |
| 5,415,842 A | 5/1995 | Maule |
| 5,418,136 A | 5/1995 | Miller et al. |
| 5,424,219 A | 6/1995 | Jirikowski |
| 5,428,690 A | 6/1995 | Bacus et al. |
| 5,432,057 A | 7/1995 | Litman et al. |
| 5,436,161 A | 7/1995 | Bergström et al. |
| 5,445,971 A | 8/1995 | Rohr |
| 5,451,683 A | 9/1995 | Barrett et al. |
| 5,455,475 A | 10/1995 | Josse et al. |
| 5,464,741 A | 11/1995 | Hendrix |
| 5,466,574 A | 11/1995 | Liberti et al. |
| 5,467,778 A | 11/1995 | Catt et al. |
| 5,468,606 A | 11/1995 | Bogart et al. |
| 5,482,830 A | 1/1996 | Bogart et al. |
| 5,482,867 A | 1/1996 | Barrett et al. |
| 5,484,867 A | 1/1996 | Lichtenhan et al. |
| 5,489,678 A | 2/1996 | Fodor et al. |
| 5,489,988 A | 2/1996 | Ackley et al. |
| 5,492,840 A | 2/1996 | Malmqvist et al. |
| 5,500,350 A | 3/1996 | Baker et al. |
| 5,504,013 A | 4/1996 | Senior |
| 5,508,171 A | 4/1996 | Walling et al. |
| 5,510,481 A | 4/1996 | Bednarski et al. |
| 5,512,131 A | 4/1996 | Kumar et al. |
| 5,514,559 A | 5/1996 | Markert-Hahn et al. |
| 5,514,785 A | 5/1996 | Van Ness et al. |
| 5,516,635 A | 5/1996 | Ekins et al. |
| 5,518,689 A | 5/1996 | Dosmann et al. |
| 5,518,883 A | 5/1996 | Soini |
| 5,527,711 A | 6/1996 | Tom-Moy et al. |
| 5,534,132 A | 7/1996 | Vreeke et al. |
| 5,554,541 A | 9/1996 | Malmqvist et al. |
| 5,569,608 A | 10/1996 | Sommer |
| 5,571,684 A | 11/1996 | Lawrence et al. |
| 5,573,909 A | 11/1996 | Singer et al. |
| 5,573,919 A | 11/1996 | Kearns et al. |
| 5,585,279 A | 12/1996 | Davidson |
| 5,589,401 A | 12/1996 | Hansen et al. |
| 5,591,581 A | 1/1997 | Massey et al. |
| 5,591,645 A | 1/1997 | Rosenstein |
| 5,596,414 A | 1/1997 | Tyler |
| 5,599,668 A | 2/1997 | Stimpson et al. |
| 5,602,040 A | 2/1997 | May et al. |
| 5,610,077 A | 3/1997 | Davis et al. |
| 5,618,888 A | 4/1997 | Choi et al. |
| 5,620,850 A | 4/1997 | Bamdad et al. |
| 5,622,871 A | 4/1997 | May et al. |
| 5,637,509 A | 6/1997 | Hemmilä et al. |
| 5,647,994 A | 7/1997 | Tuunanen et al. |
| 5,656,503 A | 8/1997 | May et al. |
| 5,658,443 A | 8/1997 | Yamamoto et al. |
| 5,663,213 A | 9/1997 | Jones et al. |
| 5,670,381 A | 9/1997 | Jou et al. |
| 5,672,256 A | 9/1997 | Yee |
| 5,700,636 A | 12/1997 | Sheiness et al. |
| 5,714,389 A | 2/1998 | Charlton et al. |
| 5,726,064 A | 3/1998 | Robinson et al. |
| 5,731,147 A | 3/1998 | Bard et al. |
| 5,736,188 A | 4/1998 | Alcock et al. |
| 5,753,517 A | 5/1998 | Brooks et al. |
| 5,770,416 A | 6/1998 | Lihme et al. |

| | | | | | | |
|---|---|---|---|---|---|---|
| 5,780,308 | A | 7/1998 | Ching et al. | 6,271,040 B1 | 8/2001 | Buechler |
| 5,788,863 | A | 8/1998 | Milunic | 6,274,324 B1 | 8/2001 | Davis et al. |
| 5,795,470 | A | 8/1998 | Wang et al. | 6,281,006 B1 | 8/2001 | Heller et al. |
| 5,795,543 | A | 8/1998 | Poto et al. | 6,284,472 B1 | 9/2001 | Wei et al. |
| 5,798,273 | A | 8/1998 | Shuler et al. | 6,287,783 B1 | 9/2001 | Maynard et al. |
| 5,811,526 | A | 9/1998 | Davidson | 6,287,871 B1 | 9/2001 | Herron et al. |
| 5,827,748 | A | 10/1998 | Golden | 6,294,391 B1 | 9/2001 | Badley et al. |
| 5,834,226 | A | 11/1998 | Maupin | 6,294,392 B1 | 9/2001 | Kuhr et al. |
| 5,837,429 | A | 11/1998 | Nohr et al. | 6,306,665 B1 | 10/2001 | Buck et al. |
| 5,837,546 | A | 11/1998 | Allen et al. | D450,854 S | 11/2001 | Lipman et al. |
| 5,843,692 | A | 12/1998 | Phillips et al. | 6,331,438 B1 | 12/2001 | Aylott et al. |
| 5,852,229 | A | 12/1998 | Josse et al. | 6,348,186 B1 | 2/2002 | Sutton et al. |
| 5,876,944 | A | 3/1999 | Kuo | 6,352,862 B1 | 3/2002 | Davis et al. |
| 5,885,527 | A | 3/1999 | Buechler | 6,362,011 B1 | 3/2002 | Massey et al. |
| 5,906,921 | A | 5/1999 | Ikeda et al. | 6,368,873 B1 | 4/2002 | Chang et al. |
| 5,910,447 | A | 6/1999 | Lawrence et al. | 6,368,875 B1 | 4/2002 | Geisberg |
| 5,910,940 | A | 6/1999 | Guerra | 6,387,707 B1 | 5/2002 | Seul et al. |
| 5,922,537 | A | 7/1999 | Ewart et al. | 6,391,558 B1 | 5/2002 | Henkens et al. |
| 5,922,550 | A | 7/1999 | Everhart et al. | 6,399,295 B1 | 6/2002 | Kaylor et al. |
| 5,945,281 | A | 8/1999 | Prabhu | 6,399,397 B1 | 6/2002 | Zarling et al. |
| 5,951,492 | A | 9/1999 | Douglas et al. | 6,399,398 B1 | 6/2002 | Cunningham et al. |
| 5,962,995 | A | 10/1999 | Avnery | 6,407,492 B1 | 6/2002 | Avnery et al. |
| 5,989,924 | A | 11/1999 | Root et al. | 6,411,439 B2 | 6/2002 | Nishikawa |
| 5,989,926 | A | 11/1999 | Badley et al. | 6,413,410 B1 | 7/2002 | Hodges et al. |
| 5,998,221 | A | 12/1999 | Malick et al. | 6,436,651 B1 | 8/2002 | Everhart et al. |
| 6,004,530 | A | 12/1999 | Sagner et al. | 6,436,722 B1 | 8/2002 | Clark et al. |
| 6,013,531 | A | 1/2000 | Wang et al. | 6,444,423 B1 | 9/2002 | Meade et al. |
| 6,020,047 | A | 2/2000 | Everhart | 6,448,091 B1 | 9/2002 | Massey et al. |
| 6,027,904 | A | 2/2000 | Devine et al. | 6,451,607 B1 | 9/2002 | Lawrence et al. |
| 6,027,944 | A | 2/2000 | Robinson et al. | 6,455,861 B1 | 9/2002 | Hoyt |
| 6,030,792 | A | 2/2000 | Otterness et al. | 6,461,496 B1 | 10/2002 | Feldman et al. |
| 6,030,840 | A | 2/2000 | Mullinax et al. | 6,468,741 B1 | 10/2002 | Massey et al. |
| 6,033,574 | A | 3/2000 | Siddiqi | 6,472,226 B1 | 10/2002 | Barradine et al. |
| 6,048,623 | A | 4/2000 | Everhart et al. | 6,479,146 B1 | 11/2002 | Caruso et al. |
| 6,057,165 | A | 5/2000 | Mansour | 6,509,085 B1 | 1/2003 | Kennedy |
| 6,060,256 | A | 5/2000 | Everhart et al. | 6,511,814 B1 | 1/2003 | Carpenter |
| 6,077,669 | A | 6/2000 | Little et al. | 6,524,864 B2 | 2/2003 | Fernandez de Castro |
| 6,080,391 | A | 6/2000 | Tsuchiya et al. | 6,556,299 B1 | 4/2003 | Rushbrooke et al. |
| 6,084,683 | A | 7/2000 | Bruno et al. | 6,566,508 B2 | 5/2003 | Bentsen et al. |
| 6,087,184 | A | 7/2000 | Magginetti et al. | 6,573,040 B2 | 6/2003 | Everhart et al. |
| 6,099,484 | A | 8/2000 | Douglas et al. | 6,579,673 B2 | 6/2003 | McGrath et al. |
| 6,103,537 | A | 8/2000 | Ullman et al. | 6,582,930 B1 | 6/2003 | Ponomarev et al. |
| 6,117,090 | A | 9/2000 | Caillouette | 6,585,939 B1 | 7/2003 | Dapprich |
| 6,130,100 | A | 10/2000 | Jobling et al. | 6,613,583 B1 | 9/2003 | Richter et al. |
| 6,133,048 | A | 10/2000 | Penfold et al. | 6,617,488 B1 | 9/2003 | Springer et al. |
| 6,136,549 | A | 10/2000 | Feistel | 6,627,459 B1 | 9/2003 | Tung et al. |
| 6,136,611 | A | 10/2000 | Saaski et al. | 6,653,149 B1 | 11/2003 | Tung et al. |
| 6,139,961 | A | 10/2000 | Blankenship et al. | 6,669,908 B2 | 12/2003 | Weyker et al. |
| 6,151,110 | A | 11/2000 | Markart | 6,670,115 B1 | 12/2003 | Zhang |
| 6,156,271 | A | 12/2000 | May | RE38,430 E | 2/2004 | Rosenstein |
| 6,165,798 | A | 12/2000 | Brooks | 6,720,007 B2 | 4/2004 | Walt et al. |
| 6,171,780 | B1 | 1/2001 | Pham et al. | 6,787,368 B1 | 9/2004 | Wong et al. |
| 6,171,870 | B1 | 1/2001 | Freitag | 6,815,218 B1 | 11/2004 | Jacobson et al. |
| 6,174,646 | B1 | 1/2001 | Hirai et al. | 6,951,631 B1 | 10/2005 | Catt et al. |
| 6,177,281 | B1 | 1/2001 | Manita | 7,044,919 B1 | 5/2006 | Catt et al. |
| 6,180,288 | B1 | 1/2001 | Everhart et al. | 7,052,831 B2 | 5/2006 | Fletcher et al. |
| 6,183,972 | B1 | 2/2001 | Kuo et al. | 7,247,500 B2 | 7/2007 | Wei et al. |
| 6,184,042 | B1 | 2/2001 | Neumann et al. | 2001/0055776 A1 | 12/2001 | Greenwalt |
| 6,187,269 | B1 | 2/2001 | Lancesseru et al. | 2002/0042149 A1 | 4/2002 | Butlin et al. |
| 6,194,220 | B1 | 2/2001 | Malick et al. | 2002/0045273 A1 | 4/2002 | Butlin et al. |
| 6,200,820 | B1 | 3/2001 | Hansen et al. | 2002/0070128 A1 | 6/2002 | Beckmann |
| 6,221,238 | B1 | 4/2001 | Grundig et al. | 2002/0146754 A1 | 10/2002 | Kitawaki et al. |
| 6,221,579 | B1 | 4/2001 | Everhart et al. | 2002/0164659 A1 | 11/2002 | Rao et al. |
| 6,234,974 | B1 | 5/2001 | Catt et al. | 2003/0017615 A1 | 1/2003 | Sidwell et al. |
| 6,235,241 | B1 | 5/2001 | Catt et al. | 2003/0119202 A1 | 6/2003 | Kaylor et al. |
| 6,235,471 | B1 | 5/2001 | Knapp et al. | 2003/0119204 A1 | 6/2003 | Wei et al. |
| 6,235,491 | B1 | 5/2001 | Connolly | 2003/0124739 A1 | 7/2003 | Song et al. |
| 6,241,863 | B1 | 6/2001 | Monbouquette | 2003/0178309 A1 | 9/2003 | Huang et al. |
| 6,242,268 | B1 | 6/2001 | Wieder et al. | 2004/0014073 A1 | 1/2004 | Trau et al. |
| 6,255,066 | B1 | 7/2001 | Louderback | 2004/0043502 A1 | 3/2004 | Song et al. |
| 6,261,779 | B1 | 7/2001 | Barbera-Guillem et al. | 2004/0043507 A1 | 3/2004 | Song et al. |
| 6,268,222 | B1 | 7/2001 | Chandler et al. | 2004/0043512 A1 | 3/2004 | Song et al. |
| 6,270,637 | B1 | 8/2001 | Crismore et al. | 2004/0106190 A1 | 6/2004 | Yang et al. |

| | | | |
|---|---|---|---|
| 2004/0121334 A1 | 6/2004 | Wei et al. |
| 2004/0197819 A1 | 10/2004 | Yang et al. |
| 2004/0197820 A1 | 10/2004 | Wei et al. |
| 2005/0112703 A1 | 5/2005 | Song |
| 2005/0112779 A1 | 5/2005 | Wei et al. |
| 2005/0112780 A1 | 5/2005 | Song |
| 2005/0136500 A1 | 6/2005 | Yang et al. |
| 2005/0136529 A1 | 6/2005 | Yang et al. |
| 2005/0136550 A1 | 6/2005 | Yang et al. |
| 2005/0191704 A1 | 9/2005 | Boga et al. |
| 2005/0244953 A1 | 11/2005 | Cohen |

FOREIGN PATENT DOCUMENTS

| | | | |
|---|---|---|---|
| EP | 0205698 A1 | 12/1986 |
| EP | 0420053 A1 | 4/1991 |
| EP | 0437287 B1 | 7/1991 |
| EP | 0462376 B1 | 12/1991 |
| EP | 0539035 A2 | 4/1993 |
| EP | 0539035 B1 | 4/1993 |
| EP | 0657737 A2 | 6/1995 |
| EP | 0657737 A3 | 6/1995 |
| EP | 0660114 B1 | 6/1995 |
| EP | 0703454 A1 | 3/1996 |
| EP | 0711414 B1 | 5/1996 |
| EP | 0724156 A1 | 7/1996 |
| EP | 0745843 A2 | 12/1996 |
| EP | 0745843 A3 | 12/1996 |
| EP | 0833159 A2 | 4/1998 |
| EP | 0859230 A1 | 8/1998 |
| EP | 0898169 B1 | 2/1999 |
| EP | 1221616 A1 | 7/2002 |
| GB | 2273772 A | 6/1994 |
| WO | WO 8804777 A1 | 6/1988 |
| WO | WO 9005305 A1 | 5/1990 |
| WO | WO 9105999 A2 | 5/1991 |
| WO | WO 9221769 A1 | 12/1992 |
| WO | WO 9221770 A1 | 12/1992 |
| WO | WO 9221975 A1 | 12/1992 |
| WO | WO 9301308 A1 | 1/1993 |
| WO | WO 9319370 A1 | 9/1993 |
| WO | WO 9406012 A1 | 3/1994 |
| WO | WO 9413835 A1 | 6/1994 |
| WO | WO 9415193 A1 | 7/1994 |
| WO | WO 9626435 A1 | 8/1996 |
| WO | WO 9709620 A1 | 3/1997 |
| WO | WO 9737222 A1 | 10/1997 |
| WO | WO 9810334 A1 | 3/1998 |
| WO | WO 9815831 A1 | 4/1998 |
| WO | WO 9827417 A1 | 6/1998 |
| WO | WO 9843086 A1 | 10/1998 |
| WO | WO 9910742 A1 | 3/1999 |
| WO | WO 9930131 A1 | 6/1999 |
| WO | WO 9936777 A1 | 7/1999 |
| WO | WO 9964864 A1 | 12/1999 |
| WO | WO 0019199 A1 | 4/2000 |
| WO | WO 0023805 A1 | 4/2000 |
| WO | WO 0034781 A1 | 6/2000 |
| WO | WO 0036416 A1 | 6/2000 |
| WO | WO 0046839 A2 | 8/2000 |
| WO | WO 0046839 A3 | 8/2000 |
| WO | WO 0047983 A1 | 8/2000 |
| WO | WO 0050891 A1 | 8/2000 |
| WO | WO 0078917 A1 | 12/2000 |
| WO | WO 0129559 A1 | 4/2001 |
| WO | WO 0138873 A2 | 5/2001 |
| WO | WO 0150129 A2 | 7/2001 |
| WO | WO 0150129 A3 | 7/2001 |
| WO | WO 0163299 A1 | 8/2001 |
| WO | WO 0171344 A2 | 9/2001 |
| WO | WO 0198765 A1 | 12/2001 |
| WO | WO 0198785 A2 | 12/2001 |
| WO | WO 02077646 A1 | 10/2002 |
| WO | WO 03005013 A1 | 1/2003 |
| WO | WO 03058246 A1 | 7/2003 |

OTHER PUBLICATIONS

Abstract of DE10024145A1, Nov. 22, 2001.
Abstract of EP0469377, Feb. 5, 1992.
Abstract of EP0617285, Sep. 28, 1994.
Abstract of Japanese Patent No. JP 8062214, Mar. 8, 1996.
*AMI Screen Printers*—Product Information, 4 pages, 1990.
Article—*A conductometral biosensor for biosecurity*, Zarini Muhammad-Tahir and Evangelyn C. Alocilja, Biosensors & Bioelectronics, vol. 18, 2003, pp. 813-819.
Article—*A Disposable Amperometric Sensor Screen Printed on a Nitrocellulose Strip: A Glucose Biosensor Employing Lead Oxide as an Interference-Removing Agent*, Gang Cui, San Jin Kim, Sung Hyuk Choi, Hakhyun Nam, and Geun Sig Cha, Analytical Chemistry, vol. 72, No. 8, Apr. 15, 2000, pp. 1925-1929.
Article—*A Fully Active Monolayer Enzyme Electrode Derivatized by Antigen-Antibody Attachment*, Christian Bourdillon, Christopher Demaille, Jean Gueris, Jacques Moiroux, and Jean-Michel Savéant, J. Am. Chem. Soc., vol. 115, No. 26, 1993, pp. 12264-12269.
Article—*A New Tetradentate β-Diketonate-Europium Chelate That Can Be Covalently Bound to Proteins for Time-Resolved Fluoroimmunoassay*, Jingli Yuan and Kazuko Matsumoto, Analytical Chemistry, vol. 70, No. 3, Feb. 1, 1998, pp. 596-601.
Article—*A Thermostable Hydrogen Peroxide Sensor Based on "Wiring" of Soybean Peroxidase*, Mark S. Vreeke, Khin Tsun Yong, and Adam Heller, Analytical Chemistry, vol. 67, No. 23, Dec. 1, 1995, pp. 4247-4249.
Article—*Acoustic Plate Waves for Measurements of Electrical Properties of Liquids*, U. R. Kelkar, F. Josse, D. T. Haworth, and Z. A. Shana, Micromechanical Journal, vol. 43, 1991, pp. 155-164.
Article—*Amine Content of Vaginal Fluid from Untreated and Treated Patients with Nonspecific Vaginitis*, Kirk C.S. Chen, Patricia S. Forsyth, Thomas M. Buchanan, and King K. Holmes, J. Clin. Invest., vol. 63, May 1979, pp. 828-835.
Article—*Analysis of electrical equivalent circuit of quartz crystal resonator loaded with viscous conductive liquids*, Journal of Electroanalytical Chemistry, vol. 379, 1994, pp. 21-33.
Article—*Application of rod-like polymers with ionophores as Langmuir-Blodgett membranes for Si-based ion sensors*, Sensors and Actuators B, 1992, pp. 211-216.
Article—*Attempts of Mimic Docking Processes of the Immune System: Recognition of Protein Multilayers*, W. Müller, H. Ringsdorf, E. Rump, G. Wildburg, X. Zhang, L. Angermaier, W. Knoll, M. Liley, and J. Spinke, Science, vol. 262, Dec. 10, 1993, pp. 1706-1708.
Article—*Biochemical Diagnosis of Vaginitis: Determination of Diamines in Vaginal Fluid*, Kirk C.S. Chen, Richard Amsel, David A. Eschenbach, and King K. Holmes, The Journal of Infectious Diseases, vol. 145, No. 3, Mar. 1982, pp. 337-345.
Article—*Biospecific Adsorption of Carbonic Anhydrase to Self-Assembled Monolayers of Alkanethiolates That Present Benzenesulfonamide Groups on Gold*, Milan Mrksich, Jocelyn R. Grunwell, and George M. Whitesides, J. Am. Chem. Soc., vol. 117, No. 48, 1995, pp. 12009-12010.
Article—*Direct Observation of Streptavidin Specifically Adsorbed on Biotin-Functionalized Self-Assembled Monolayers with the Scanning Tunneling Microscope*, Lukas Häussling, Bruno Michel, Helmut Ringsdorf, and Heinrich Rohrer, Angew Chem. Int. Ed. Engl., vol. 30, No. 5, 1991, pp. 569-572.
Article—*Electrical Surface Perturbation of a Piezoelectric Acoustic Plate Mode by a Conductive Liquid Loading*, Fabien Josse, IEEE Transactions on Ultrasonics, Ferroelectrics, and Frequency Control, vol. 39, No. 4, Jul. 1992, pp. 512-518.
Article—*Europium Chelate Labels in Time-Resolved Fluorescence Immunoassays and DNA Hybridization Assays*, Eleftherios P. Diamandis and Theodore K. Christopoulos, Analytical Chemistry, vol. 62, No. 22, Nov. 15, 1990, pp. 1149-1157.
Article—*Evaluation of a Time-Resolved Fluorescence Microscope Using a Phosphorescent Pt-Porphine Model System*, E. J. Hennink, R. de Haas, N. P. Verwoerd, and H. J. Tanke, Cytometry, vol. 24, 1996, pp. 312-320.

Article—*Fabrication of Patterned, Electrically Conducting Polypyrrole Using a Self-Assembled Monolayer: A Route to All-Organic Circuits*, Christopher B. Gorman, Hans A. Biebuyck, and George M. Whitesides, American Chemical Society, 1992, 2 pages.

Article—*Fabrication of Surfaces Resistant to Protein Adsorption and Application to Two-Dimensional Protein Patterning*, Suresh K. Bhatia, John L. Teixeira, Mariquita Anderson, Lisa C. Shriver-Lake, Jeffrey M. Calvert, Jacque H. Georger, James J. Hickman, Charles S. Dulcey, Paul E. Schoen, and Frances S. Ligler, Analytical Biochemistry, vol. 208, 1993, pp. 197-205.

Article—*Features of gold having micrometer to centimeter dimensions can be formed through a combination of stamping with an elastomeric stamp and an alkanethiol "ink" followed by chemical etching*, Amit Kumar and George M. Whitesides, Appl. Phys. Lett., vol. 63, No. 14, Oct. 4, 1993, pp. 2002-2004.

Article—*Fine Structure of Human Immunodeficiency Virus (HIV) and Immunolocalization of Structural Proteins*, Hans R. Gelderblom, Elda H.S. Hausmann, Muhsin Özel, George Pauli, and Meinrad A. Koch, Virology, vol. 156, No. 1, Jan. 1987, pp. 171-176.

Article—*Generation of electrochemically deposited metal patterns by means of electron beam (nano)lithography of self-assembled monolayer resists*, J. A. M. Sondag-Hethorst, H. R. J. van-Helleputte, and L. G. J. Fokkink, Appl. Phys. Lett., vol. 64, No. 3, Jan. 17, 1994, pp. 285-287.

Article—*Heterogeneous Enzyme Immunoassay of Alpha-Fetoprotein in Maternal Serum by Flow-Injection Amperometric Detection of 4-Aminophenol*, Yan Xu, H. Brian Haisall, and William R. Heineman, Clinical Chemistry, vol. 36, No. 11, 1990, pp. 1941-1944.

Article—*Hollow latex particles: synthesis and applications*, Charles J. McDonald and Michael J. Devon, Advances in Colloid and Interface Science, Vo. 99, 2002, pp. 181-213.

Article—*How to Build a Spectrofluorometer*, Spex Fluorolog 3, Horiba Group, 2001, pp. 1-14.

Article—*Hydrogen Peroxide and β-Nicotinamide Adenine Dinucleotide Sensing Amperometric Electrodes Based on Electrical Connection of Horseradish Peroxidase Redox Centers to Electrodes Through a Three-Dimensional Electron Relaying Polymer Network*, Mark Vreeke, Ruben Maidan, and Adam Heller, Analytical Chemistry, vol. 64, No. 24, Dec. 15, 1992, pp. 3084-3090.

Article—*Immunoaffinity Based Phosphorescent Sensor Platform for the Detection of Bacterial Spores*, Peter F. Scholl, C. Brent Bargeron, Terry E. Phillips, Tommy Wong, Sala Abubaker, John D. Groopman, Paul T. Strickland, and Richard C. Benson, Proceedings of SPIE, vol. 3913, 2000, pp. 204-214.

Article—*Inert Phosphorescent Nanospheres as Markers for Optical Assays*, Jens M. Kürner, Ingo Klimant, Christian Krause, Harald Preu, Werner Kunz, and Otto S. Wolfbeis, Bioconjugate Chem., vol. 12, No. 6, 2001, pp. 883-889.

Article—*Intelligent Gels*, Yoshihito Osada and Simon B. Ross-Murphy, Scientific American, May 1993, pp. 82-87.

Article—*Latex Immunoassays*, Leigh B. Bangs, Journal of Clinical Immunoassay, vol. 13, No. 3, 1990, pp. 127-131.

Article—*Longwave luminescent porphyrin probes*, Dmitry B. Papkovsky, Gelii P. Ponomarev, and Otto S. Wolfbeis, Spectrochimica Acta Part A 52, 1996, pp. 1629-1638.

Article—*Mechanical resonance gas sensors with piezoelectric excitation and detection using PVDF polymer foils*, R. Block, G. Fickler, G. Lindner, H. Müller, and M. Wohnhas, Sensors and Actuators B, 1992, pp. 596-601.

Article—*Microfabrication by Microcontact Printing Of Self-Assembled Monolyaers*, James L. Wilbur, Armit Kumar, Enoch Kim, and George M. Whitesides, Advanced Materials, vol. 6, No. 7/8, 1994, pp. 600-604.

Article—*Modification of monoclonal and polyclonal IgG with palladium (II) coproporphyrin I: stimulatory and inhibitory functional effects induced by two different methods*, Sergey P. Martsev, Valery A. Preygerzon, Yanina I. Mel'nikova, Zinaida I. Kravchuk, Gely V. Ponomarev, Vitaly E. Lunev, and Alexander P. Savitsky, Journal of Immunological Methods 186, 1996, pp. 293-304.

Article—*Molecular Design Temperature-Responsive Polymers as Intelligent Materials*, Teruo Okano, Advances in Polymer Science, 1992, pp. 179-197.

Article—*Molecular Gradients of w-Substituted Alkanethiols on Gold: Preparation and Characterization*, Bo Liedberg and Pentti Tengvall, Langmuir, vol. 11, No. 10, 1995, pp. 3821-3827.

Article—*Monofunctional Derivatives of Coproporphyrins for Phosphorescent Labeling of Proteins and Binding Assays*, Tomás C. O'Riordan, Aleksi E. Soini, and Dmitri B. Papkovsky, Analytical Biochemistry, vol. 290, 2001, pp. 366-375.

Article—*Near Infrared Phosphorescent Metalloporphrins*, Alexander P. Savitsky Anna V. Savitskaja, Eugeny A. Lukjanetz, Svetlana N. Dashkevich, and Elena A. Makarova, SPIE, vol. 2980, 2001, pp. 352-357.

Article—*New Approach To Producing Patterned Biomolecular Assemblies*, Suresh K. Bhatia, James J. Hickman, and Frances S. Ligler, J. Am. Chem. Soc., vol. 114, 1992, pp. 4433-4434.

Article—*New Use of Cyanosilane Coupling Agent for Direct Binding of Antibodies to Silica Supports. Physicochemical Characterization of Molecularly Bioengineered Layers*, Sandrine Falipou, Jean-Marc Chovelon, Claude Martelet, Jacqueline Margonari and Dominique Cathignol, Bioconjugate Chem., vol. 10, No. 3, 1999, pp. 346-353.

Article—*On the use of ZX-LiNbO$_3$ acoustic plate mode devices as detectors for dilute electrolytes*, F. Josse, Z. A. Shana, D. T. Haworth, and S. Liew, Sensors and Actuators B, vol. 9, 1992, pp. 92-112.

Article—*One-step all-in-one dry reagent immunoassays with fluorescent europium chelate label and time-resolved fluorometry*, Timo Lövgren, Liisa Meriö, Katja Mitrunen, Maija-Liisa Mäkinen, Minna Mäkelä, Kaj Blomberg, Tom Palenius, and Kim Pettersson, Clinical Chemistry 42:8, 1996, pp. 1196-1201.

Article—*Optical Biosensor Assay (OBA™)*, Y. G. Tsay, C. I. Lin, J. Lee, E. K. Gustafson, R. Appelqvist, P. Magginetti, R. Norton, N. Teng, and D. Charlton, Clinical Chemistry, vol. 37, No. 9, 1991, pp. 1502-1505.

Article—*Order in Microcontact Printed Self-Assembled Monolayers*, N. B. Larsen, H. Biebuyck, E. Delamarche, and B. Michel, J. Am. Chem. Soc., vol. 119, No. 13, 1997, pp. 3017-3026.

Article—*Orientation dependence of surface segregation in a dilute Ni-Au alloy*, W. C. Johnson, N. G. Chavka, R. Ku, J. L. Bomback, and P. P. Wynblatt, J. Vac. Sci. Technol. vol. 15, No. 2, Mar./Apr. 1978, pp. 467-469.

Article—*Patterned Condensation Figures as Optical Diffraction Gratings*, Amit Kumar and George M. Whitesides, Science, vol. 263, Jan. 7, 1994, pp. 60-62.

Article—*Patterned Functionalization of Gold and Single Crystal Silicon via Photochemical Reaction of Surface-Confined Derivatives of $(n^5$ -$C_5H_5)Mn(CO)_3$*, Doris Kang and Mark S. Wrighton, Langmuir, vol. 7, No. 10, 1991, pp. 2169-2174.

Article—*Patterned Metal Electrodeposition Using an Alkanethiolate Mask*, T. P. Moffat and H. Yang, J. Electrochem. Soc., vol. 142, No. 11, Nov. 1995, pp. L220-L222.

Article—*Performance Evaluation of the Phosphorescent Porphyrin Label: Solid-Phase Immunoassay of α-Fetoprotein*, Tomás C. O'Riordan, Aleksi E. Soini, Juhani T. Soini, and Dmitri B. Papkovsky, Analytical Chemistry, vol. 74, No. 22, Nov. 15, 2002, pp. 5845-5850.

Article—*Phosphorescent porphyrin probes in biosensors and sensitive bioassays*, D. B. Papkovsky, T. O'Riordan, and A. Soini, Biochemical Society Transactions, vol. 28, part 2, 2001, pp. 74-77.

Article—*Photolithography of self-assembled monolayers: optimization of protecting groups by an electroanalytical method*, Jamila Jennane, Tanya Boutrous, and Richard Giasson, Can. J. Chem., vol. 74, 1996, pp. 2509-2517.

Article—*Photopatterning and Selective Electroless Metallization of Surface-Attached Ligands*, Walter J. Dressick, Charles S. Dulcey, Jacque H. Georger, Jr., and Jeffrey M. Calvert, American Chemical Society, 1992, 2 pages.

Article—*Photosensitive Self-Assembled Monolayers on Gold: Photochemistry of Surface-Confined Aryl Azide and Cyclopentadienylmanganese Tricarbonyl*, Eric W. Wollman, Doris Kang, C. Daniel Frisbie, Ivan M. Lorkovic and Mark S. Wrighton, J. Am. Chem. Soc., vol. 116, No. 10, 1994, pp. 4395-4404.

Article—*Polymer Based Lanthanide Luminescent Sensors for the Detection of Nerve Agents*, Amanda L. Jenkins, O. Manuel Uy, and George M. Murray, Analytical Communications, vol. 34, Aug. 1997, pp. 221-224.

Article—*Prediction of Segregation to Alloy Surfaces from Bulk Phase Diagrams*, J. J. Burton and E. S. Machlin, Physical Review Letters, vol. 37, No. 21, Nov. 22, 1976, pp. 1433-1436.

Article—*Principle and Applications of Size-Exclusion Chromatography*, Impact Analytical, 1979, pp. 1-3.

Article—*Probing of strong and weak electrolytes with acoustic wave fields*, R. Dahint, D. Grunze, F. Josse, and J. C. Andle, Sensors and Actuators B, vol. 9, 1992, pp. 155-162.

Article—*Production of Hollow Microspheres from Nanostructured Composite Particles*, Frank Caruso, Rachel A. Caruso, and Helmuth MöhwaldChem, Mater., vol. 11, No. 11, 1999, pp. 3309-3314.

Article—*Quantitative Prediction of Surface Segregation*, M. P. Seah, Journal of Catalysts, vol. 57, 1979, pp. 450-457.

Article—*Quartz Crystal Resonators as Sensors in Liquids Using the Acoustoelectric Effect*, Zack A. Shana and Fabian Josse, Analytical Chemistry, vol. 66, No. 13, Jul. 1, 1994, pp. 1955-1964.

Article—*Responsive Gels: Volume Transitions I*, M. Ilavský, H. Inomata, A. Khokhlove, M. Konno, A. Onuki, S. Saito, M. Shibayama, R.A. Siegel, S. Starodubtzev, T. Tanaka, and V. V. Vasiliveskaya, Advances in Polymer Science, vol. 109, 1992, 9 pages.

Article—*Room-Temperature Phosphorescent Palladium—Porphine Probe for DNA Determination*, Montserrat Roza-Fernández, Maria Jesús Valencia-González, and Marta Elena Diaz-Garcia, Analytical Chemistry, vol. 69, No. 13, Jul. 1, 1997, pp. 2406-2410.

Article—*Self-Assembled Monolayer Films For Nanofabrication*, Elizabeth A. Dobisz, F. Keith Perkins, Susan L. Brandow, Jeffrey M. Calvert, and Christie R. K. Marrian, Mat. Res. Soc. Symp. Proc., vol. 380, 1995, pp. 23-34.

Article—*Sensing liquid properties with thickness-shear mode resonators*, S. J. Martin, G. C. Frye, and K. O. Wessendorf, Sensors and Actuators A, vol. 44, 1994, pp. 209-218.

Article—*Separation-Free Sandwich Enzyme Immunoassays Using Microporous Gold Electrodes and Self-Assembled Monolayer/Immobilized Capture Antibodies*, Chuanming Duan and Mark E. Meyerhoff, Analytical Chemistry, vol. 66, No. 9, May 1, 1994, pp. 1369-1377.

Article—*Solid Substrate Phosphorescent Immunoassay Based On Bioconjugated Nanoparticles*, Baoquan Sun, Guangshun Yi, Shuying Zhao, Depu Chen, Yuxiang Zhou, and Jing Cheng, Analytical Letters, vol. 34, No. 10, 2001, pp. 1627-1637.

Article—*Stimuli-Responsive Poly(N-isopropylacrylamide) Photo- and Chemical-Induced Phase Transitions*, Advances in Polymer Science, 1994, pp. 50-65.

Article—*The Adsorptive Characteristics of Proteins for Polystyrene and Their Significance in Solid-Phase Immunoassays*, L. A. Cantaero, J. E. Butler, and J. W. Osborne, Analytical Biochemistry, vol. 105, 1980, pp. 375-382.

Article—*The Use of Self-Assembled Monolayers and a Selective Etch To Generate Patterned Gold Features*, Amit Kumar, Hans A. Biebuyck, Nicholas L. Abbott, and George M. Whitesides, Journal of the American Chemical Society, vol. 114, 1992, 2 pages.

Article—*Volume Phase Transition of N-Alkylacrylamide Gels*, S. Saito, M. Konno, and H. Inomata, Advances in Polymer Science, vol. 109, 1992, pp. 207-232.

Article—*Whole Blood Capcellia CD4/CD8 Immunoassay for Enumeration of CD4+ and CD8+ Peripheral T Lymphocytes*, Dominique Carrière, Jean Pierre Vendrell, Claude Fontaine, Aline Jansen, Jacques Reynes, Isabelle Pagès, Catherine Holzmann, Michel Laprade, and Bernard Pau, Clinical Chemistry, vol. 45, No. 1, 1999, pp. 92-97.

CELQUAT® SC-230M (28-6830), CELQUAT® SC-240C and SC-230M, from National Starch & Chemical, 2001, 1 page.

CELQUAT® SC-230M (28-6830), Polyquaternium-10, from National Starch & Chemical, 2001, 1 page.

*Dualite® Polymeric Microspheres*, from Pierce & Stevens Corp. a subsidiary of Sovereign Specialty Chemicals, Inc., 2001, 2 pages.

*Dynabeads® Biomagnetic Separation Technology—The Principle* from Dynal Biotech, 1998, 2 pages.

*ECCOSPHERES® glass microspheres—hollow glass microspheres* from Emerson & Cuming Composite Materials, Inc., 1998, 1 page.

*Factors influencing the formation of hollow ceramic microspheres by water extraction of colloidal droplets*, J. Mater. Res., vol. 10, No. 1, 1996, p. 84.

*Flow-Based Microimmunoassay*, Analytical Chemistry, vol. 73, No. 24, Mark A. Hayes, Nolan A. Polson, Allison, N. Phayre, and Antonia A. Garcia, Dec. 15, 2001, pp. 5896-5902.

*Fluorescent Microsphere Standards for Flow Cytometry and Fluorescence Microscopy* from Molecular Probes, 2001, pp. 1-8.

*FluoSpheres® Fluorescent Microspheres*, Production Information from Molecular Probes, Mar. 13, 2001, pp. 1-6.

*Magnetic Microparticles*, Polysciences, Inc. Technical Data Sheet 438, 2 pages, publication undated.

*Making sun exposure safer for everyone* from Rohm and Haas Company (Bristol Complex), 2001, 2 pages.

*Nanostructured™ Chemicals: Bridging the Gap Between Fillers, Surface Modifications and Reinforcement*, Joseph D. Lichtenhan, Invited lectures: Functional Tire Fillers 2001, Ft. Lauderdale, FL, Jan. 29-31, 2001, pp. 1-15.

Pamphlet—The ClearPlan® Easy Fertility Monitor.

*POSS Polymer Systems* from Hybrid Plastics, 3 pages.

*The colloidal state*, Introduction to Colloid and Surface Chemistry, $4^{th}$ Ed., 17 pages.

*Working With FluoSpheres® Fluorescent Microspheres*, Properties and Modifications, Production Information from Molecular Probes, Mar. 9, 2001, pp. 1-5.

Related U.S. Patent Application Form.

MEMBRANE-BASED ASSAY DEVICES

RELATED APPLICATIONS

The present application is a divisional of U.S. application Ser. No. 10/228,836 filed on Aug. 27, 2002, which is incorporated herein in its entirety by reference thereto.

BACKGROUND OF THE INVENTION

Various analytical procedures and devices are commonly employed in assays to determine the presence and/or absence of analytes in a test sample. For instance, immunoassays utilize mechanisms of the immune systems, wherein antibodies are produced in response to the presence of antigens that are pathogenic or foreign to the organisms. These antibodies and antigens, i.e., immunoreactants, are capable of binding with one another, thereby causing a highly specific reaction mechanism that can be used to determine the presence or concentration of that particular antigen in a biological sample.

There are several well-known immunoassay methods that use immunoreactants labeled with a detectable component so that the analyte can be detected analytically. For example, "sandwich-type" assays typically involve mixing the test sample with antibodies to the analyte. These antibodies are mobile and linked to a label or probe, such as dyed latex, a colloidal metal sol, or a radioisotope. This mixture is then contacted with a chromatographic medium containing a band or zone of immobilized antibodies to the analyte. The chromatographic medium is often in the form of a strip resembling a dipstick. When the complex of the analyte and the labeled antibody reaches the zone of the immobilized antibodies on the chromatographic medium, binding occurs and the bound labeled antibodies are localized at the zone. This indicates the presence of the analyte. This technique can be used to obtain quantitative or semi-quantitative results. Some examples of such sandwich-type assays are described by U.S. Pat. Nos. 4,168,146 to Grubb, et al. and 4,366,241 to Tom, et al.

An alternative technique is the "competitive-type" assay. In a "competitive-type" assay, the label is typically a labeled analyte or analyte-analogue that competes for binding of an antibody with any unlabeled analyte present in the sample. Competitive assays are typically used for detection of analytes such as haptens, each hapten being monovalent and capable of binding only one antibody molecule. Examples of competitive immunoassay devices are described in U.S. Pat. Nos. 4,235,601 to Deutsch, et al., 4,442,204 to Liotta, and 5,208,535 to Buechler, et al.

Magnetic binding assays have been widely used for separation of biological species (e.g., proteins, cells, and microorganisms) from complex samples because they can be easily manipulated by magnetic fields and require no special and expensive instruments. In this manner, magnetic immunoassays can provide a fast and simple technique to determine the presence or absence of the species. In such assays, various signal-generating mechanisms have been used, including color (absorption and reflectance), fluorescence, chemiluminescence, radioactivity and enzymes.

However, conventional magnetic immunoassays generally require control samples to generate a calibration curve each time they are used to obtain quantitative information for analytes. Specifically, when analyzing the presence or absence of a biological species within a test sample, multiple control samples are simultaneously tested for known amounts of the species in an attempt to calibrate the test assay at approximately the same conditions. Unfortunately, this calibration technique is often inconvenient, costly, and cumbersome on the tester.

As such, a need currently exists for an accurate calibration system for assays that is readily controllable and relatively inexpensive.

SUMMARY OF THE INVENTION

In accordance with one embodiment of the present invention, a membrane-based device (e.g., lateral flow membrane-based assay device) is disclosed for detecting the presence or quantity of an analyte residing in a test sample. The device comprises a porous membrane in fluid communication with detection probes capable of generating a detection signal and magnetic calibration probes capable of generating a calibration signal. Generally speaking, the detection probes and calibration probes may be formed from any material that is capable of generating a detectable signal. For example, in some embodiments, such probes are selected from the group consisting of chromogens, catalysts, fluorescent compounds, chemiluminescent compounds, phosphorescent compounds, radioactive compounds, direct visual labels, liposomes, and combinations thereof. For instance, the detection probes and calibration probes may be fluorescent compounds, such as fluorescent particles. In one particular embodiment, the detection probes are fluorescent non-magnetic compounds and the calibration probes are fluorescent magnetic particles. If desired, the fluorescent magnetic particles may be conjugated with a specific binding member or blocked.

In some embodiments, the device further comprises one or more conjugate pads in fluid communication with the porous membrane. If desired, the detection probes and calibration probes are applied to one or more of the conjugate pads. The device may further comprise a sampling pad in fluid communication with the porous membrane. If desired, the test sample is applied to the sampling pad. Further, the device may also comprise a wicking pad in fluid communication with the porous membrane to facilitate in the flow of the test sample therethrough.

A magnetic device is positioned adjacent to a detection zone defined by the porous membrane. The magnetic device is capable of separating the detection probes and calibration probes from a test sample applied to the porous membrane. For example, in one embodiment of a sandwich assay format, the detection probes and calibration probes form complexes with the analyte. When placed into communication with the magnetic device at the detection zone, these analyte complexes and any uncomplexed calibration probes are separated from the remaining test sample.

The separated detection and calibration probes (complexed and/or uncomplexed) are thus capable of indicating the presence or quantity of analyte in the test sample. Specifically, the amount of the analyte within the test sample is proportional to the intensity of the detection signal generated by the separated detection probes (complexed and/or uncomplexed) at the detection zone calibrated by the intensity of the calibration signal generated by the separated calibration probes (complexed and/or uncomplexed) at the detection zone. For example, in one embodiment, the amount of the analyte within the test sample is proportional to the intensity of the detection signal divided by the intensity of the calibration signal.

In accordance with another embodiment of the present invention, a method for detecting the presence or quantity of an analyte residing in a test sample is disclosed. The method comprises:

i) providing a membrane-based device that comprises:
   a) a porous membrane in fluid communication with detection probes capable of generating a detection signal and magnetic calibration probes capable of generating a calibration signal, the porous membrane defining a detection zone; and
   b) a magnetic device positioned adjacent to the detection zone;

ii) contacting the detection probes and calibration probes with the test sample to form a solution;

iii) separating the detection probes and the calibration probes from the solution at the detection zone using the magnetic device;

iv) exciting the separated detection probes (complexed and/or uncomplexed) and the separated calibration probes (complexed and/or uncomplexed), wherein the excitation causes the separated detection probes to emit the detection signal and the separated calibration probes to emit the calibration signal;

v) measuring the intensity of the detection signal at a first emission wavelength and the intensity of the calibration signal at a second emission wavelength, which may be the same or different than the first emission wavelength; and vi) comparing the intensity of the detection signal to the calibration signal, wherein the amount of the analyte within the test sample is proportional to the intensity of the detection signal calibrated by the intensity of the calibration signal.

The separated detection probes and calibration probes may be excited simultaneously or separately. Likewise, the intensity of the detection signal and the calibration signal may be measured simultaneously or separately. Further, in one embodiment, the method further comprises generating a calibration curve by plotting the intensity of the detection signal calibrated by the intensity of the calibration signal for a plurality of predetermined analyte concentrations.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
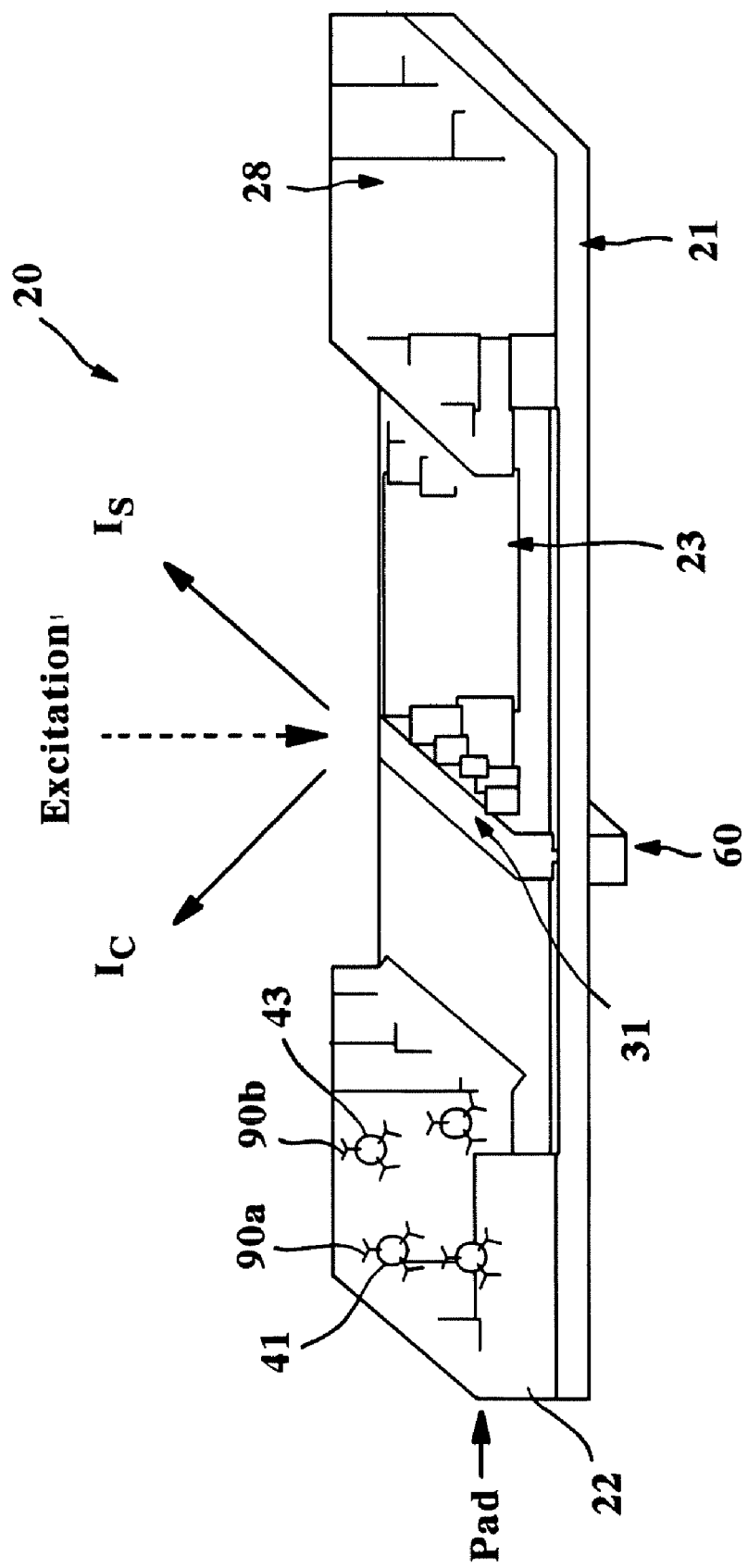
FIG. 1 is a perspective view of one embodiment of a membrane-based device of the present invention.

Repeat use of reference characters in the present specification and drawings is intended to represent same or analogous features or elements of the invention.

DETAILED DESCRIPTION OF REPRESENTATIVE EMBODIMENTS

Definitions

As used herein, the term "analyte" generally refers to a substance to be detected. For instance, analytes can include antigenic substances, haptens, antibodies, and combinations thereof. Analytes include, but are not limited to, toxins, organic compounds, proteins, peptides, microorganisms, amino acids, nucleic acids, hormones, steroids, vitamins, drugs (including those administered for therapeutic purposes as well as those administered for illicit purposes), bacteria, virus particles and metabolites of or antibodies to any of the above substances. Specific examples of some analytes include ferritin; creatinine kinase MIB (CK-MB); digoxin; phenyloin; phenobarbitol; carbamazepine; vancomycin; gentamycin; theophylline; valproic acid; quinidine; leutinizing hormone (LH); follicle stimulating hormone (FSH); estradiol, progesterone; IgE antibodies; vitamin B2 micro-globulin; glycated hemoglobin (Gly. Hb); cortisol; digitoxin; N-acetylprocainamide (NAPA); procainamide; antibodies to rubella, such as rubella-IgG and rubella IgM; antibodies to toxoplasmosis, such as toxoplasmosis IgG (Toxo-IgG) and toxoplasmosis IgM (Toxo-IgM); testosterone; salicylates; acetaminophen; hepatitis B virus surface antigen (HBsAg); antibodies to hepatitis B core antigen, such as anti-hepatitis B core antigen IgG and IgM (Anti-HBC); human immune deficiency virus 1 and 2 (HIV 1 and 2); human T-cell leukemia virus 1 and 2 (HTLV); hepatitis B e antigen (HBeAg); antibodies to hepatitis B e antigen (Anti-HBe); thyroid stimulating hormone (TSH); thyroxine (T4); total triiodothyronine (Total T3); free triiodothyronine (Free T3); carcinoembryonic antigen (CEA); and alpha fetal protein (AFP). Drugs of abuse and controlled substances include, but are not intended to be limited to, amphetamine; methamphetamine; barbiturates, such as amobarbital, secobarbital, pentobarbital, phenobarbital, and barbital; benzodiazepines, such as librium and valium; cannabinoids, such as hashish and marijuana; cocaine; fentanyl; LSD; methaqualone; opiates, such as heroin, morphine, codeine, hydromorphone, hydrocodone, methadone, oxycodone, oxymorphone and opium; phencyclidine; and propoxyphene. Other potential analytes may be described in U.S. Pat. No. 4,366,241 to Tom et al.

As used herein, the term "test sample" generally refers to a material suspected of containing the analyte. The test sample can be used directly as obtained from the source or following a pretreatment to modify the character of the sample. The test sample can be derived from any biological source, such as a physiological fluid, including, blood, saliva, ocular lens fluid, cerebral spinal fluid, sweat, urine, milk, ascites fluid, raucous, synovial fluid, peritoneal fluid, amniotic fluid or the like. The test sample can be pretreated prior to use, such as preparing plasma from blood, diluting viscous fluids, and the like.

Methods of treatment can involve filtration, distillation, concentration, inactivation of interfering components, and the addition of reagents. Besides physiological fluids, other liquid samples can be used such as water, food products and the like for the performance of environmental or food production assays. In addition, a solid material suspected of containing the analyte can be used as the test sample. In some instances it may be beneficial to modify a solid test sample to form a liquid medium or to release the analyte.

DETAILED DESCRIPTION

Reference now will be made in detail to various embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention covers such modifications and variations as come within the scope of the appended claims and their equivalents.

In general, the present invention is directed to a membrane-based assay for detecting the presence or quantity of an analyte residing in a test sample. The device utilizes a self-calibrated magnetic binding assay (e.g., sandwich, competitive, etc.) that includes detection probes capable of generating a detection signal (e.g., fluorescent non-magnetic particles) and calibration probes capable of generating a calibration signal (e.g., fluorescent magnetic particles). The amount of the analyte within the test sample is proportional (e.g., directly or inversely) to the intensity of the detection signal calibrated by the intensity of the calibration signal. It has been discovered that the self-calibration system provides an accurate, inexpensive, and readily controllable method of determining the presence of an analyte in a test sample.

Figure 2:
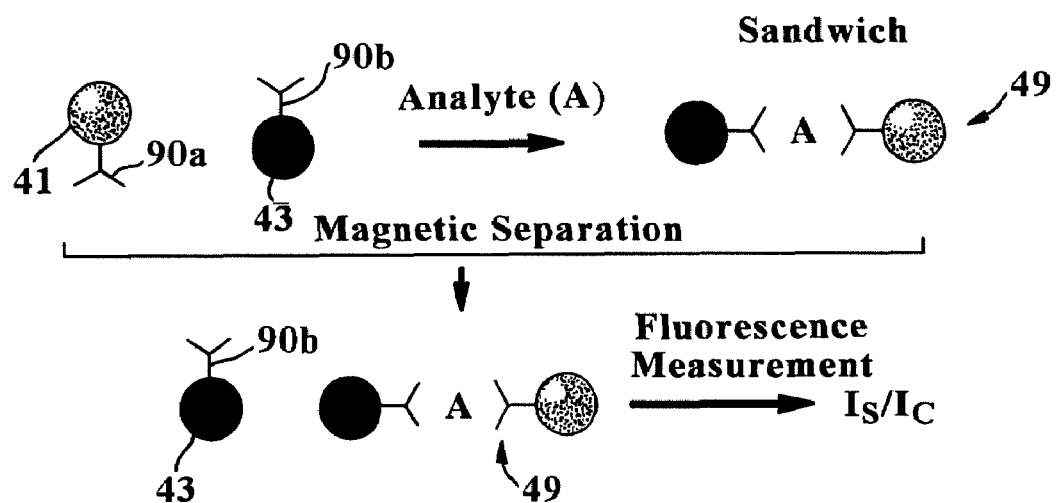
FIG. 2 is a graphical illustration of the mechanism used for one embodiment of a sandwich assay format of the present invention.

Referring to FIGS. 1-2, for instance, one embodiment of a lateral flow membrane-based device 20 that can be formed according to the present invention will now be described in more detail. As shown, the device 20 contains a porous membrane 23 optionally supported by a rigid material 21. In general, the porous membrane 23 can be made from any of a variety of materials through which the test sample is capable of passing. For example, the materials used to form the porous membrane 23 can include, but are not limited to, natural, synthetic, or naturally occurring materials that are synthetically modified, such as polysaccharides (e.g., cellulose materials such as paper and cellulose derivatives, such as cellulose acetate and nitrocellulose); silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and the like. In one particular embodiment, the porous membrane 23 is formed from nitrocellulose and/or polyester sulfone materials. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms.

The device 20 may also contain a wicking pad 28. The wicking pad 28 generally receives fluid that has migrated through the entire porous membrane 23. As is well known in the art, the wicking pad 28 can assist in promoting capillary action and fluid flow through the membrane 23.

To initiate the detection of an analyte within the test sample, a user may directly apply the test sample to a portion of the porous membrane 23 through which it can then travel to reach one or more detection and calibration zones (described below). Alternatively, the test sample may first be applied to a sampling pad (not shown) that is in fluid communication with the porous membrane 23. Some suitable materials that can be used to form the sampling pad include, but are not limited to, nitrocellulose, cellulose, porous polyethylene pads, and glass fiber filter paper. If desired, the sampling pad may also contain one or more assay pretreatment reagents, either diffusively or non-diffusively attached thereto.

In the illustrated embodiment, the test sample travels from the sampling pad (not shown) to a conjugate pad 22 that is placed in communication with one end of the sampling pad. The conjugate pad 22 is formed from a material through which the test sample is capable of passing. For example, in one embodiment, the conjugate pad 22 is formed from glass fibers. Although only one conjugate pad 22 is shown, it should be understood that other conjugate pads may also be used in the present invention.

To facilitate detection of the presence or absence of an analyte within the test sample, various detection probes 41 may be applied to the conjugate pad 22. While contained on the conjugate pad 22, these probes 41 remain available for binding with the analyte as it passes from the sampling pad through the conjugate pad 22. Upon binding with the analyte, the probes 41 can later serve to identify the presence or absence of the analyte. The detection probes 41 may be used for both detection and calibration of the device 20. In alternative embodiments, however, separate calibration probes 43 can also be applied to the conjugate pad 22 for use in conjunction with the detection probes 41 to facilitate simultaneous calibration and detection, thereby eliminating inaccuracies often created by conventional assay calibration systems. It should be understood, however, that the detection probes 41 and/or the calibration probes 43 may be applied together or separately at any location of the device 20, and need not be applied to the conjugate pad 22. Further, it should also be understood that the detection probes 41 and/or the calibration probes 43 may be applied to the same or different conjugate pads.

Any substance generally capable of generating a signal that is detectable visually or by an instrumental device may be used as the detection probes 41 and/or the calibration probes 43. Various suitable substances can include chromogens; catalysts; fluorescent compounds; chemiluminescent compounds; phosphorescent compounds; radioactive compounds; direct visual labels, including colloidal metallic (e.g., gold) and non-metallic particles, dye particles, enzymes or substrates, or organic polymer latex particles; liposomes or other vesicles containing signal producing substances; and the like. For instance, some enzymes suitable for use as probes are disclosed in U.S. Pat. No. 4,275,149 to Litman, et al., which is incorporated herein in its entirety by reference thereto for all purposes. One example of an enzyme/substrate system is the enzyme alkaline phosphatase and the substrate nitro blue tetrazolium-5-bromo-4-chloro-3-indolyl phosphate, or derivative or analog thereof, or the substrate 4-methylumbelliferyl-phosphate. Other suitable probes may be described in U.S. Pat. Nos. 5,670,381 to Jou, et al. and 5,252,459 to Tarcha, et al., which are incorporated herein in their entirety by reference thereto for all purposes.

In some embodiments, the detection probes 41 and/or the calibration probes 43 can contain a fluorescent compound that produces a detectable signal. The fluorescent compounds can be fluorescent molecules, polymers, dendrimers, particles, and the like. Some examples of suitable fluorescent molecules, for instance, include, but are not limited to, fluorescein, europium chelates, phycobiliprotein, rhodamine and their derivatives and analogs. Moreover, some commercially available examples of suitable fluorescent particles include fluorescent carboxylated microspheres sold by Molecular Probes, Inc. under the trade names "FluoSphere" (Red 580/605) and "TransfluoSphere" (543/620), as well as "Texas Red" and 5- and 6-carboxytetramethylrhodamine, which are also sold by Molecular Probes, Inc.

Regardless of the technique used to impart the probe with a signal generating capability, it is typically desired that the detection probes 41 and/or the calibration probes 43 be magnetically responsive probes. Generally, a material is considered "magnetically responsive" or "magnetic" if it is influenced by the application of a magnetic field, such as, for example, if it is attracted or repulsed or has a detectable magnetic susceptibility or induction. For instance, some examples of suitable magnetically responsive materials that can be used to impart magnetic properties to a probe include, but are not limited to, paramagnetic materials, superparamagnetic materials, ferromagnetic materials, ferrimagnetic materials, and metamagnetic materials. Specific examples are metals such as iron, nickel, cobalt, chromium, manganese, and the like; lanthanide elements such as neodymium, erbium, and the like; alloys such as magnetic alloys of aluminum, nickel, cobalt, copper and the like; oxides such as ferric oxide ($Fe_3O_4$), ferrous oxide ($Fe_2O_3$), chromium oxide ($CrO_2$), cobalt oxide (CoO), nickel oxide ($NiO_2$), manganese oxide ($Mn_2O_3$) and the like; composite materials such as ferrites and the like; and solid solutions such as magnetite with ferric oxide and the like.

In some embodiments, the detection probes 41 and/or the calibration probes 43 are fluorescent and magnetic. Fluorescent magnetic probes are generally well known in the art and often include a magnetically responsive component and a fluorescent component. In some embodiments, for example, one or more fluorescent dyes can be applied to magnetic particles to form the probes, while in other embodiments, fluorescent dye(s) can be applied to non-magnetic particles that are coupled with magnetic particles. Some examples of suitable fluorescent dyes include, but are not limited to, monomethine dyes, trimethine dyes, pentamethine dyes, quinoline dyes, squaric acid-based dyes, and the like. The monomethine dyes that are pyridines typically have a blue or blue-green fluorescence emission, while quinolines typically have a green or yellow-green fluorescence emission. The trimethine dyes are substantially shifted toward red wavelengths, while the pentamethine dyes are shifted even further, often exhibiting infrared fluorescence emission. Specific examples of such fluorescent dyes include, but are not limited to, phthalocyanines, 2,3-naphthalocyanines, squaraines and croconic acid derivatives. Other examples of suitable fluorescent magnetic particles are believed to be described in U.S. Pat. Nos. 4,731,337 to Luotola, et al., and 6,268,222 to Chandler, et al., which are incorporated herein in their entirety by reference thereto for all purposes.

When the detection probes 41 and/or the calibration probes 43 are particles, such as described above, the mean diameter of the particulate probes may generally vary as desired depending on factors such as the type of particle chosen, the pore size of the membrane, and the membrane composition. For example, in some embodiments, the mean diameter of the particulate probes can range from about 0.01 microns to about 1,000 microns, in some embodiments from about 0.01 microns to about 100 microns, and in some embodiments, from about 0.01 microns to about 10 microns. In one particular embodiment, the particulate probes have a mean diameter of from about 1 to about 2 microns. Generally, the particles are substantially spherical in shape, although other shapes including, but not limited to, plates, rods, bars, irregular shapes, etc., are suitable for use in the present invention. As will be appreciated by those skilled in the art, the composition, shape, size, and/or density of the particles may widely vary.

The detection probes 41 and/or the calibration probes 43 may be capable of bonding (covalently or non-covalently) or physically adsorbing the analyte. However, it is often desired to modify the probes in some manner so that they are more readily able to bond to the analyte. In such instances, the detection probes 41 and/or the calibration probes 43 can be modified with certain specific binding members 90a and/or 90b (See FIG. 2) that are adhered thereto to form probe conjugates.

Specific binding members generally refer to a member of a specific binding pair, i.e., two different molecules where one of the molecules chemically and/or physically binds to the second molecule. For instance, immunoreactive specific binding members can include antigens, haptens, aptamers, antibodies, and complexes thereof, including those formed by recombinant DNA methods or peptide synthesis. An antibody can be a monoclonal or polyclonal antibody, a recombinant protein or a mixture(s) or fragment(s) thereof, as well as a mixture of an antibody and other specific binding members. The details of the preparation of such antibodies and their suitability for use as specific binding members are well known to those skilled in the art.

Other common specific binding pairs include but are not limited to, biotin and avidin, carbohydrates and lectins, complementary nucleotide sequences (including probe and capture nucleic acid sequences used in DNA hybridization assays to detect a target nucleic acid sequence), complementary peptide sequences including those formed by recombinant methods, effector and receptor molecules, hormone and hormone binding protein, enzyme cofactors and enzymes, enzyme inhibitors and enzymes, and the like. Furthermore, specific binding pairs can include members that are analogs of the original specific binding member. For example, a derivative or fragment of the analyte, i.e., an analyte-analog, can be used so long as it has at least one epitope in common with the analyte.

Figure 6:
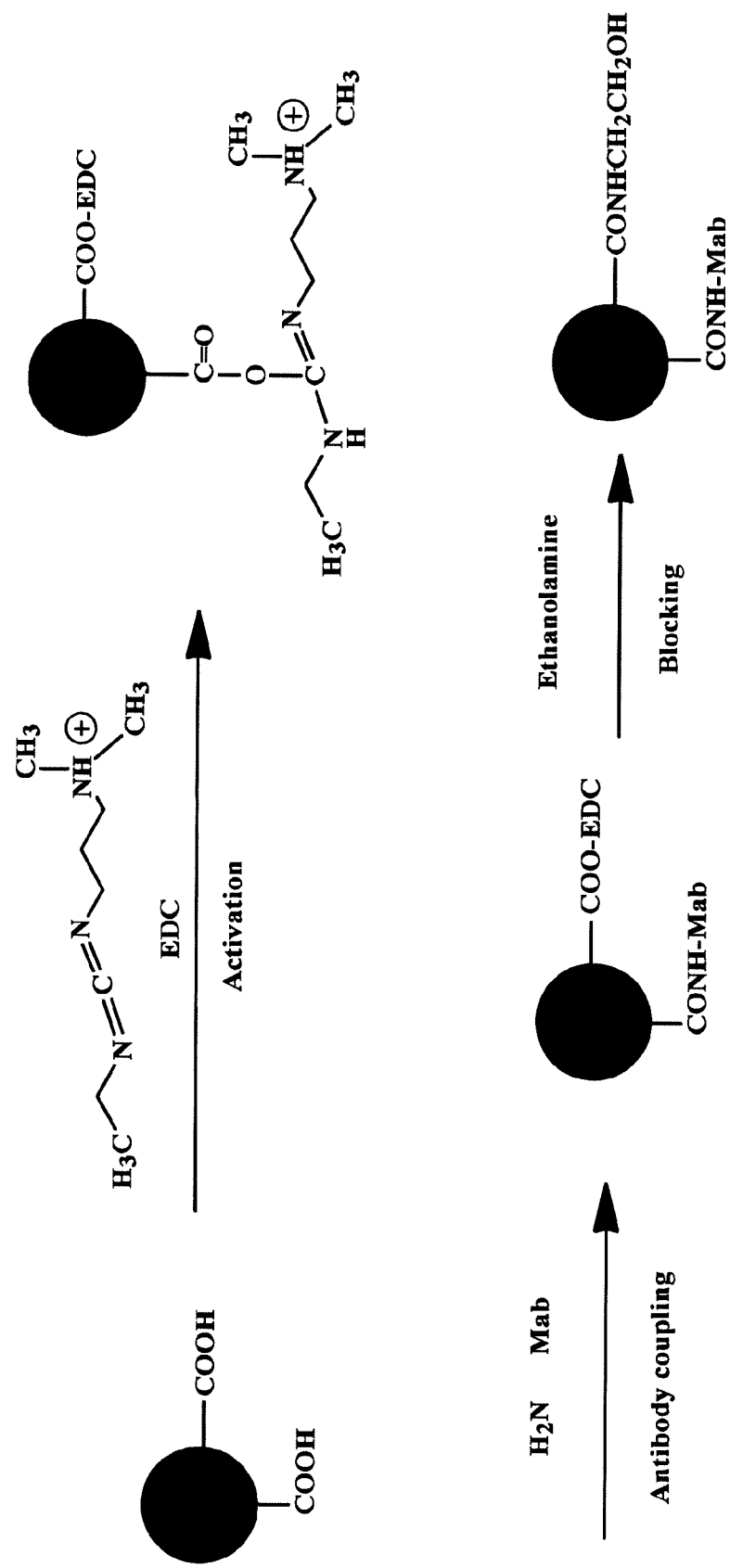
FIG. 6 is a graphical illustration of one embodiment for covalently conjugating an antibody to carboxylate nanoparticles.

The specific binding members 90a and/or 90b can generally be attached to the probes 41 and/or 43 using any of a variety of well-known techniques. For instance, covalent attachment of the specific binding members 90a and/or 90b to the probes 41 and/or 43 (e.g., microparticles) can be accomplished using carboxylic, amino, aldehyde, bromoacetyl, iodoacetyl, thiol, epoxy and other reactive or linking functional groups, as well as residual free radicals and radical cations, through which a protein coupling reaction can be accomplished. A surface functional group can also be incorporated as a functionalized co-monomer because the surface of the microparticle can contain a relatively high surface concentration of polar groups. In addition, although microparticle probes are often functionalized after synthesis, in certain cases, such as poly(thiophenol), the microparticles are capable of direct covalent linking with a protein without the need for further modification. For example, referring to FIG. 6, one embodiment of the present invention for covalently conjugating a probe is illustrated. As shown, the first step of conjugation is activation of carboxylic groups on the probe surface using carbodiimide. In the second step, the activated carboxylic acid groups are reacted with an amino group of an antibody to form an amide bond. The activation and/or antibody coupling can occur in a buffer, such as phosphate-buffered saline (PBS) (e.g., pH of 7.2) or 2-(N-morpholino) ethane sulfonic acid (MES) (e.g., pH of 5.3). As shown, the resulting probes can then be blocked with ethanolamine, for instance, to form the probe conjugate. Besides covalent bonding, other attachment techniques, such as adsorption, may also be utilized in the present invention.

Referring again to FIGS. 1-2, a test sample containing an analyte can initially be applied to the sampling pad. From the sampling pad, the test sample can then travel to the conjugate pad 22, where the analyte mixes with the detection probes 41 and/or the calibration probes 43. Depending on the type of probes selected, the analyte may bind with the detection probes 41 and/or the calibration probes 43 to form complexes 49 (See FIG. 2). For instance, in one embodiment, a test sample containing an analyte is mixed with (1) fluorescent non-magnetic particles 41 conjugated with a first binding member 90a and (2) fluorescent magnetic particles 43 conjugated with a second binding member 90b. In such an instance, the analyte forms sandwich complexes 49 with the fluorescent non-magnetic particles 41 and the fluorescent magnetic particles 43. Moreover, because the conjugate pad 22 is in fluid communication with the porous membrane 23, the complexes 49 can migrate from the conjugate pad 22 to a detection zone 31 present on the porous membrane 23.

At the detection zone 31, the complexes 49 and any unbound conjugated, fluorescent magnetic particles 43 are then captured by a magnetic device 60 and separated from the rest of the sample using conventional techniques. A magnetic field generator, for instance, can be used to generate a magnetic field that elicits a response from the magnetically responsive probes. Suitable magnetic field generators include, but are not limited to, permanent magnets and electromagnets. The magnetic separation process typically involves mixing the sample with the magnetic particles in a liquid medium to bind the analyte by affinity reaction, and then separating the unbound magnetic particles and analyte complexes from the sample medium by applying a magnetic field. Most, if not all of the magnetic particles, except those particles that are colloidal, settle in time. The liquid medium, therefore, can be agitated to keep the particles suspended for a sufficient period of time to allow the bioaffinity binding reaction to occur. Examples of known agitation methods include shaking, swirling, rocking, rotation, or similar manipulations of a partially filled container. Some commercially available examples of suitable magnetic separation devices include the Dynal MPC series of separators manufactured by Dynal, Inc., Lake Success, N.Y., which employ a permanent magnet located externally to a container holding a test medium and provide only for separation. Mixing of the magnetic particles in the test medium for affinity binding reaction is done separately. In addition, other methods for capturing magnetic particles may be described in U.S. Pat. Nos. 5,200,084 to Liberti, et al.; 5,647,994 to Tuunanen, et al.; 5,795,470 to Wang, et al.; and 6,033,574 to Siddiqi, which are incorporated herein in their entirety by reference thereto for all purposes.

Once captured, the fluorescence signal of the fluorescent magnetic particles 43, complexed and uncomplexed, and the complexes 49 can be measured using conventional techniques. For example, in one embodiment, the particles 43 and complexes 49 can be excited with the same external source. In this embodiment, the source supplies radiation at an excitation wavelength, thereby causing the particles 43 to emit light at a wavelength that is different than the wavelength emitted by the complexes 49. This enables the presence of the complexes 49 and particles 41 to be separately measured. Alternatively, the particles 43 and complexes 49 can also be measured separately using separate external sources.

Generally speaking, fluorescence is the result of a three-stage process that occurs in certain fluorescent compounds. In the first stage, energy is supplied by an external source, such as an incandescent lamp or a laser and absorbed by the fluorescent compound, creating an excited electronic singlet state. In the second stage, the excited state exists for a finite time during which the fluorescent compound undergoes conformational changes and is also subject to a multitude of possible interactions with its molecular environment. During this time, the energy of the excited state is partially dissipated, yielding a relaxed state from which fluorescence emission originates. The third stage is the fluorescence emission stage wherein energy is emitted, returning the fluorescent compound to its ground state. The emitted energy is lower than its excitation energy (light or laser) and thus of a longer wavelength. This shift or difference in energy or wavelength allows the emission energy to be detected and isolated from the excitation energy.

Fluorescence detection generally utilizes wavelength filtering to isolate the emission photons from the excitation photons, and a detector that registers emission photons and produces a recordable output, usually as an electrical signal or a photographic image. There are generally four recognized types of detectors: spectrofluorometers and microplate readers; fluorescence microscopes; fluorescence scanners; and flow cytometers. One suitable fluorescence detector for use with the present invention is a FluoroLog III Spectrofluorometer, which is sold by SPEX Industries, Inc. of Edison, N.J.

Figure 7:
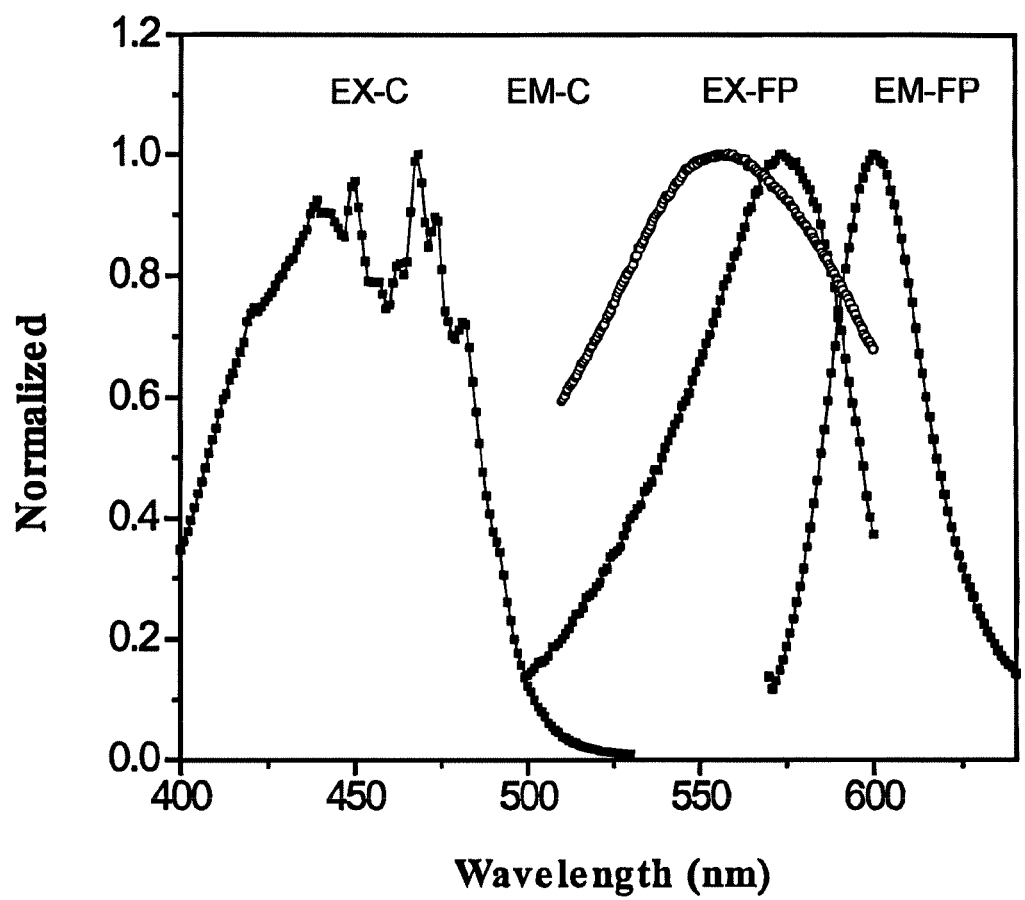
FIG. 7 shows the excitation (EX) and emission (EM) spectra of a calibration probe (C) and a detection probe (FP) in accordance with one embodiment of the present invention.

Although not required, the selection criteria of particularly desired detection and calibration probe pairs include: (1) little or no spectral overlap for either the absorption spectra or the fluorescence spectra so that emission intensities can be measured separately; (2) no significant fluorescent energy transfer between the detection and calibration probes when brought into a close proximity so that they emit independently; and (3) relatively long emission wavelength (e.g., greater than about 600 nm) so that the autofluorescence of biological fluids has a minimal effect on the fluorescence measurement. FIG. 7, for example, illustrates an exemplary calibration probe and detection probe having excitation spectra with little overlap so that they can be independently excited.

Further, if desired, a technique known as "time-resolved fluorescence detection" may also be utilized in the present invention. Time-resolved fluorescence detection is designed to reduce background signals from the emission source or from scattering processes (resulting from scattering of the excitation radiation) by taking advantage of the fluorescence characteristics of certain fluorescent materials, such as lanthanide chelates of europium (Eu (III)) and terbium (Tb (III)). Such chelates can exhibit strongly red-shifted, narrow-band, long-lived emission after excitation of the chelate at substantially shorter wavelengths. Typically, the chelate possesses a strong ultraviolet absorption band due to a chromophore located close to the lanthanide in the molecule. Subsequent to light absorption by the chromophore, the excitation energy can be transferred from the excited chromophore to the lanthanide. This is followed by a fluorescence emission characteristic of the lanthanide. The use of pulsed excitation and time-gated detection, combined with narrow-band emission filters, allows for specific detection of the fluorescence from the lanthanide chelate only, rejecting emission from other species present in the sample that are typically shorter-lived or have shorter wavelength emission. Other time-resolved techniques for measuring fluorescence are described in U.S. Pat. No. 5,585,279 to Davidson and U.S. Pat. No. 5,637,509 to Hemmila, et al., which are incorporated herein in their entirety by reference thereto for all purposes.

Regardless of the technique used to measure fluorescence, the absolute amount of the analyte can be ascertained by comparing the fluorescence signal of the captured, fluorescent non-magnetic particles 41 with the captured, fluorescent magnetic particles 43. The fluorescence intensity of the captured, fluorescent non-magnetic particles 41, $I_s$, can be compared to the fluorescence intensity of the captured, fluorescent magnetic particles 43, $I_c$. The total amount of the captured fluorescent magnetic particles 43 is predetermined and known and thus can be used for calibration purposes. For example, in one embodiment, the amount of analyte is directly proportional to the ratio of $I_s$ to $I_c$. Based upon the intensity range in which the detection zone 31 falls, the general concentration range for the analyte may be determined. As a result, calibration and sample testing may be conducted under approximately the same conditions at the same time, thus providing reliable quantitative or semi-quantitative results, with increased sensitivity.

If desired, the ratio of $I_s$ to $I_c$ may be plotted versus the analyte concentration for a range of known analyte concentrations to generate a calibration curve. To determine the quantity of analyte in an unknown test sample, the signal ratio may then be converted to analyte concentration according to the calibration curve. It should be noted that the capturing efficiency of the complexed and uncomplexed fluorescent magnetic particles is generally the same for any given sample. Accordingly, the variation in capturing efficiency is not believed to significantly interfere with the results from sample-to-sample because the ratio of fluorescence intensities (i.e., $I_s/I_c$) is used instead of absolute fluorescence. It should also be noted that alternative mathematical relationships between $I_s$ and $I_c$ may be plotted versus the analyte concentration to generate the calibration curve. For example, in one embodiment, the value of $I_s/(I_s+I_c)$ may be plotted versus analyte concentration to generate the calibration curve.

Various other embodiments are also contemplated by the present invention. For instance, referring to FIG. 3, the device 20 described above and illustrated in FIG. 1 can be modified to form another format of a sandwich assay. In one embodiment, for instance, a test sample containing an analyte can initially be mixed with (1) fluorescent non-magnetic particles 141a conjugated with a first binding member 190a, (2) fluorescent magnetic particles 143, and (3) non-fluorescent magnetic particles 141b conjugated with a second binding member 190b. In this particular embodiment, the fluorescent magnetic particles 143 can be blocked with a blocking agent, such as β-casein, to prevent nonspecific binding to the analyte, thereby allowing such particles 143 to act only as a calibration probe. Further, the first specific binding member 190a and the second specific binding member 190b may be analogs of the analyte.

The term "blocking agent" means a reagent that adheres to the probe surface so that it "blocks" or prevents non-analyte materials from binding to the surface. Blockers can include, but are not limited to, β-casein, albumins such as bovine serum albumin, pluronic or other surfactants, polyethylene glycol, polyvinyl alcohol, or sulfur derivatives of the above compounds, and any other blocking material known to those of ordinary skill in the art.

Referring again to FIG. 3, the analyte forms sandwich complexes 149 with the conjugated, fluorescent non-magnetic particles 141a and the conjugated, non-fluorescent, magnetic particles 141b. Because the conjugate pad 22 is in fluid communication with the porous membrane 23, the complexes 149 can migrate from the conjugate pad 22 to the detection zone 31 present on the porous membrane 23. At the detection zone 31, the complexes 149 and any unbound particles 143 and/or 141b are then captured by the magnetic device 60 and separated from the rest of the sample. As described above, the absolute amount of the analyte can be ascertained by comparing the fluorescence intensity of the captured, fluorescent non-magnetic particles 141a, $I_s$, to the fluorescence intensity of the captured, fluorescent magnetic particles 143, $I_c$. In particular, the total amount of the captured fluorescent magnetic particles 143 is predetermined and known and thus can be used for calibration purposes. Accordingly, the amount of analyte in this embodiment is directly proportional to the ratio of $I_s$ to $I_c$.

Figure 4:
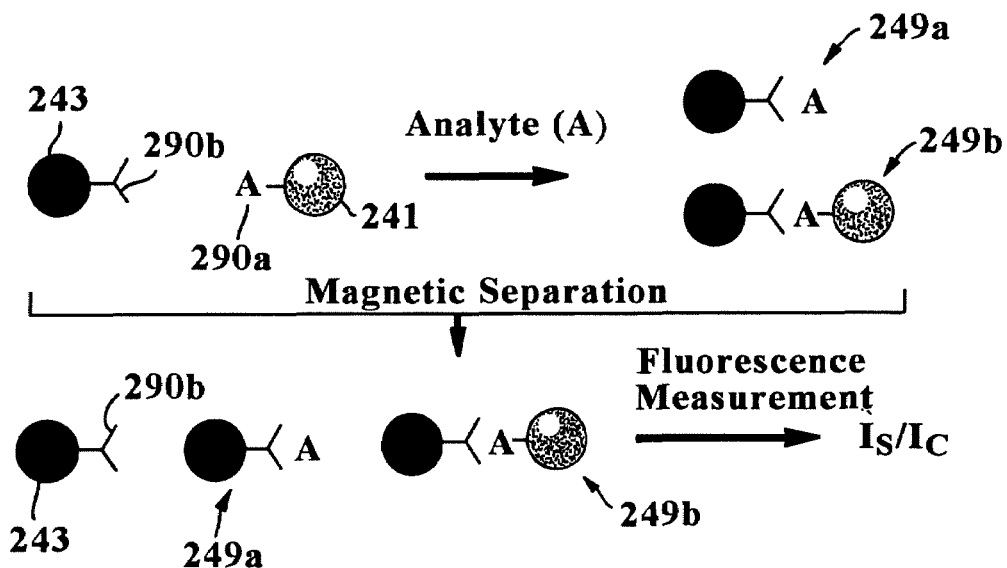
FIG. 4 is a graphical illustration of the mechanism used for one embodiment of a competitive assay format of the present invention.

Moreover, referring to FIG. 4, the device 20 described above and illustrated in FIG. 1 can be modified to form a competitive assay format. In one embodiment, for instance, a test sample containing an analyte can initially be mixed with (1) fluorescent non-magnetic particles 241 conjugated with a first binding member 290a and (2) fluorescent magnetic particles 243 conjugated with a second binding member 290b. In this particular embodiment, the first binding member 290a can be identical to the analyte, while the second binding member 290b can be an analog of the analyte.

Upon mixing, the analyte competes with the conjugated, fluorescent non-magnetic particles 241 for the conjugated, fluorescent magnetic particles 243 such that complexes 249a of the analyte and the fluorescent magnetic particles 243 and complexes 249b of the fluorescent magnetic particles 243 and the fluorescent, non-magnetic particles 241 are formed. Because the conjugate pad 22 is in fluid communication with the porous membrane 23, the complexes 249a and 249b can migrate from the conjugate pad 22 to the detection zone 31 present on the porous membrane 23. At the detection zone 31, the complexes 249a and 249b and any unbound particles 243 are then captured by the magnetic device 60 and separated from the rest of the sample. As described above, the absolute amount of the analyte can be ascertained by comparing the fluorescence intensity of the captured, fluorescent non-magnetic particles 241, $I_s$, to the fluorescence intensity of the captured, complexed or uncomplexed, fluorescent magnetic particles 243, $I_c$. In particular, the total amount of the captured fluorescent magnetic particles 243 is predetermined and known and thus can be used for calibration purposes. Accordingly, the amount of analyte in this embodiment is inversely proportional to the ratio of $I_s$ to $I_c$.

Figure 5:
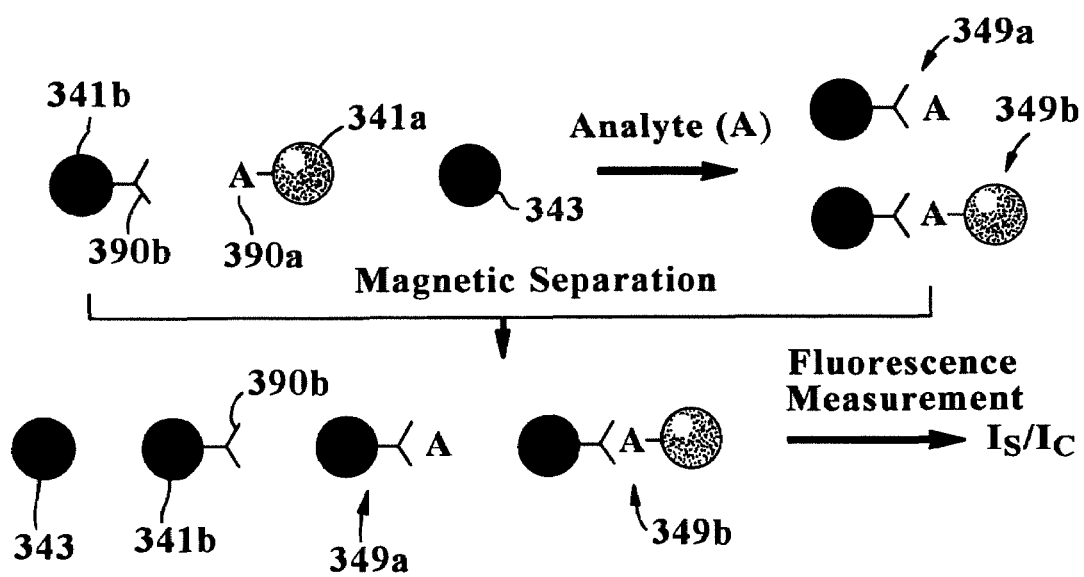
FIG. 5 is a graphical illustration of the mechanism used for another embodiment of a competitive assay format of the present invention.

Referring to FIG. 5, the device 20 described above and illustrated in FIG. 1 can also be modified to form another format of a competitive assay. In one embodiment, for instance, a test sample containing an analyte can initially be mixed with (1) fluorescent non-magnetic particles 341a conjugated with a first binding member 390a (2) fluorescent magnetic particles 343, and (3) non-fluorescent magnetic particles 341b conjugated with a second binding member 390b. In this particular embodiment, the first binding member 390a can be identical to the analyte, while the second binding member 390b can be an analog of the analyte. Further, the fluorescent magnetic particles 343 can be blocked with a blocking agent, such as β-casein, to prevent nonspecific binding to the analyte, thereby allowing such particles to act only as a calibration probe.

Upon mixing, the analyte competes with the conjugated, fluorescent non-magnetic particles 341a for the conjugated, non-fluorescent magnetic particles 341b such that complexes 349a of the analyte and the non-fluorescent magnetic particles 341b and complexes 349b of the non-fluorescent magnetic particles 341b and the fluorescent non-magnetic particles 341a are formed. Because the conjugate pad 22 is in fluid communication with the porous membrane 23, the complexes 349a and 349b can migrate from the conjugate pad 22 to the detection zone 31 present on the porous membrane 23. At the detection zone 31, the complexes 349a and 349b and any unbound particles 343 and/or 341b are then captured by the magnetic device 60 and separated from the rest of the sample. As described above, the absolute amount of the analyte can be ascertained by comparing the fluorescence intensity of the captured, fluorescent non-magnetic particles 341a, $I_s$, to the fluorescence intensity of the captured, fluorescent magnetic particles 343, $I_c$. In particular, the total amount of the captured fluorescent magnetic particles 343 is predetermined and known and thus can be used for calibration purposes. Accordingly, the amount of analyte in this embodiment is inversely proportional to the ratio of $I_s$ to $I_c$.

Although various embodiments of device configurations have been described above, it should be understood, that a device of the present invention may generally have any configuration desired, and need not contain all of the components described above. In addition, different assay formats may also be utilized for the device 20. For example, a competitive assay may be formed such as shown in FIG. 4 and described above, except that the particles 241 are fluorescent, magnetic particles and the particles 243 are fluorescent, non-magnetic particles. Likewise, a competitive assay may be formed such as shown in FIG. 5 and described above, except that the particles 341a are non-fluorescent, magnetic particles and the particles 341b are fluorescent, non-magnetic particles. Various other device configurations and/or assay formats are also described in U.S. Pat. Nos. 5,395,754 to Lambotte, et al.; 5,670,381 to Jou, et al.; and 6,194,220 to Malick, et al., which are incorporated herein in their entirety by reference thereto for all purposes.

Moreover, although various embodiments have been described above that relate specifically to the use of fluorescence as the mechanism for calibration and detection, other well known detection mechanisms are equally applicable in the present invention. For example, in some embodiments, the detection and/or calibration probes may be chemiluminescent or phosphorescent compounds. Chemiluminescent probes, for instance, may be excited through the use of a suitable reactant as is well known in the art. Still other embodiments and configurations are also contemplated by the present invention.

The present inventors have discovered that the membrane-based assay device of the present invention can be utilized to manipulate magnetic probes and establish separation and detection of an analyte. Specifically, magnetic separation and detection techniques (e.g., fluorescence) are built into an integrated system. Further, the system is self-calibrated to eliminate the requirement of control calibration samples when using conventional external calibration techniques. In one embodiment, self-calibration is accomplished through the use of fluorescent magnetic probes. The fluorescence emitted from the fluorescent magnetic probes and fluorescent non-magnetic probes can be separately measured on the same sample. Because the number of magnetic particles is predetermined, the system is self-calibrated when determining the amount of the captured fluorescent non-magnetic probes, and subsequently, the amount of analyte. Furthermore, because the fluorescence of the calibration and detection probes are simultaneously measured under identical conditions, potential interference from many variations, such as temperature and instrument instability, can be avoided to improve detection reliability and consistency.

The present invention may be better understood with reference to the following examples.

EXAMPLE 1

Figure 3:
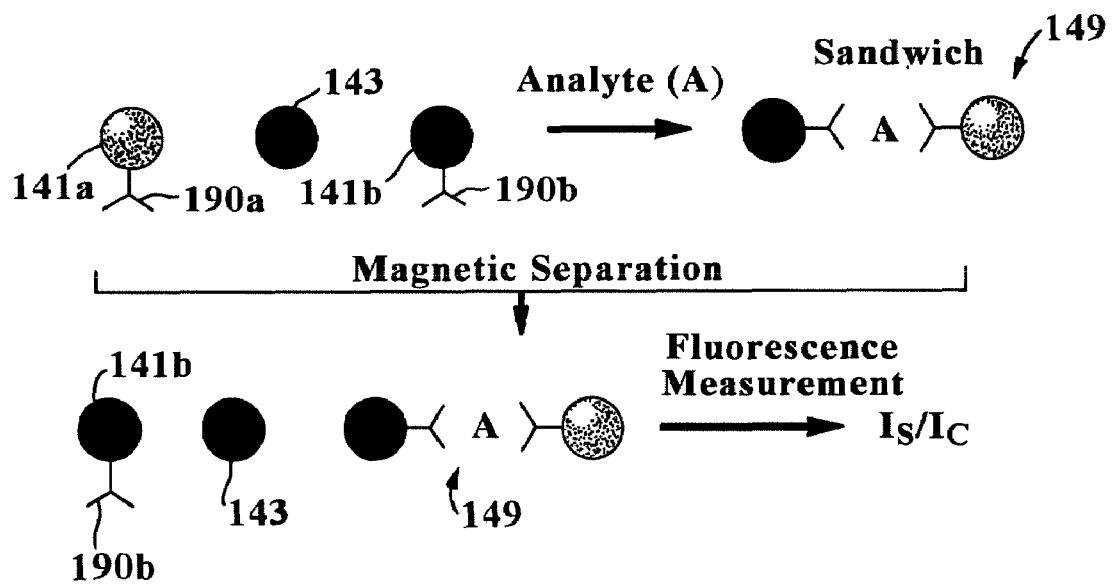
FIG. 3 is a graphical illustration of the mechanism used for another embodiment of a sandwich assay format of the present invention.

The ability to detect the presence of an analyte using a sandwich assay, such as shown in FIG. 3, was demonstrated. Initially, the following components were added to six Eppendorf vials:

(1) 25 microliters of covalently conjugated, non-fluorescent magnetic particles (3 milligrams per milliliter in PBS buffer);

(2) 15 microliters of covalently conjugated, fluorescent non-magnetic particles (2 milligrams per milliliter in PBS buffer);

(3) 10 microliters of fluorescent magnetic particles blocked by β-casein (3 milligrams per milliliter in PBS buffer); and (4) Leutinizing hormone (LH) analyte ranging from 0, 10 microliters (1 microgram per milliliter), 20 microliters (1 microgram per milliliter), 40 microliters (1 microgram per milliliter), 40 microliters (2 microgram per milliliter) and 80 microliters (2 micrograms per milliliter).

To each of the Eppendorf vials, an appropriate amount of PBS buffer was added to a final volume of 150 microliters. The samples were incubated at room temperature for 10 minutes with gentle shaking. The magnetic particles were then separated by a magnetic separator obtained from Dynal, Inc. The supernatant from each vial was discarded and the magnetic particles were re-suspended in 1.5 milliliters of PBS. 300 microliters of the fluorescent magnetic particle suspension was used for each fluorescence measurement. A "Fluorolog III Spectrofluorometer", which was obtained from SPEX Industries, Inc. of Edison, N.J., was used to measure the fluorescence of the sample using a right angle mode. An excitation wavelength of 470 nanometers and an emission wavelength of 560 nanometers were used for the fluorescent magnetic particles, while an excitation wavelength of 570 nanometers and an emission wavelength of 605 nanometers were used for the fluorescent, non-magnetic particles. The integration time was 0.2 seconds.

Figure 8:
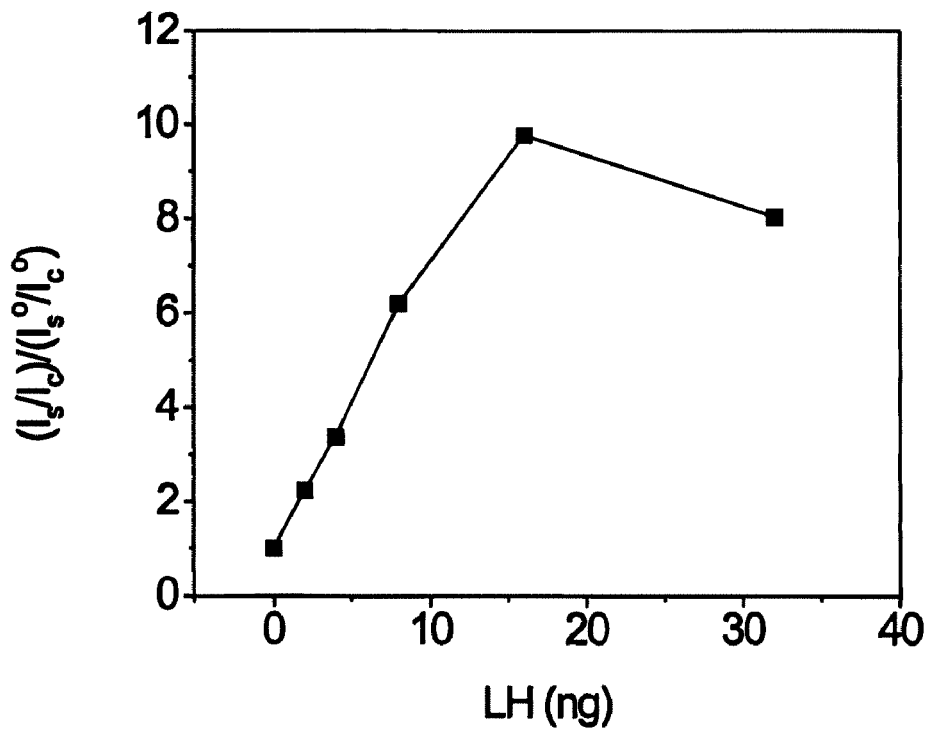
FIG. 8 shows the normalized fluorescent intensity versus the amount of leutinizing harmone (LH) as discussed in Example 1.

The normalized and calibrated fluorescence intensity as a function of the dose of LH in each sample is shown in FIG. 8. Normalized intensity was obtained by dividing the measured fluorescence intensity of the sample by the fluorescence intensity of a control sample. The control sample was the sample without the analyte.

The particles used in Example 1 were formed as follows:

Non-Fluorescent Magnetic Particles 125 microliters of 10% carboxylate-modified paramagnetic particles (0.35 microns, Estapor® Superparamagnetic microspheres, obtained from Bang's Laboratories, Inc.) were washed once with 1.5 milliliters of carbonate buffer and twice with PBS using a magnetic separator. The washed particles were re-suspended in 0.6 milliliters PBS and 15 milligrams carbodiimide (from Polysciences, Inc.). The mixture was allowed to react at room temperature (RT) for 30 minutes on a shaker. The activated particles were then washed twice with a borate buffer. The activated particles were again re-suspended in 1.2 milliliters of a borate buffer. Thereafter, 30 microliters of LH β-monoclonal antibody (9.8 mg/ml, obtained from Fitzgerald Industries International, Inc.) was added to the activated particles. The reaction mixture was allowed to react at room temperature on a shaker overnight. The activated particles were then collected and incubated in 1 milliliter of 0.1 molar ethanolamine under gentle shaking for 15 minutes. The particles were then washed twice with PBS and stored at 4° C. in a buffer that contained 0.1 molar PBS, 0.15 molar NaCl, 1% β-casein, 5% glycerol and 0.1% $NaN_3$.

Fluorescent Non-Magnetic Particles

The "fluorescent non-magnetic" particles were covalently conjugated according to the procedure described above, except that the binding member was LH α-monoclonal antibody (9.8 milligrams per milliliter, obtained from Fitzgerald Industries International, Inc.) instead of LH β-monoclonal antibody. The particles utilized were FluoSpheres® carboxylate-modified microspheres, which were obtained from Molecular Probes, Inc. The particles had a particle size of 0.5 microns, and were red fluorescent with an excitation wavelength of 580 nanometers and an emission wavelength of 605 nanometers.

Fluorescent Magnetic Particles 100 microliters of a 2.76% solids suspension of fluorescent superparamagnetic particles (obtained from Polysciences, Inc. of Warrington, Pa.) were combined with 1 milliliter of a borate buffer (0.1 molar, pH=8.5) in an Eppendorf tube. Such particles have a mean diameter of between 1 to 2 microns and are believed to be iron-containing microspheres that have a polystyrene surface that allows for passive adsorption and functional group reactions with proteins. The particles were separated by a magnetic separator obtained from Dynal, Inc. and re-suspended in 200 microliters of a 10 milligram per milliliter solution of β-casein in a 0.1 molar borate buffer. The suspension was incubated for 30 minutes with gentle mixing. The above step was repeated twice. The separated particles were re-suspended in 200 microliters of PBS and stored at 4° C.

Leutinizing Hormone (LH)

The "leutinizing hormone (LH)" was obtained from Fitzgerald Industries International, Inc.

EXAMPLE 2

The ability to detect the presence of an analyte using a sandwich assay, such as shown in FIG. 2, was demonstrated. Initially, the following components were added to six Eppendorf vials:
(1) 5 microliters of covalently conjugated, fluorescent non-magnetic particles (2 milligrams per milliliter in PBS buffer);
(2) 15 microliters of physical absorption conjugated, fluorescent magnetic particles (3 milligrams per milliliter in PBS buffer); and
(3) Leutinizing hormone (LH) analyte ranging from 0, 5, 10 microliters, 20, 40, and 100 microliters (2 micrograms per milliliter).

To each of the Eppendorf vials, an appropriate amount of PBS buffer was added to a final volume of 150 microliters. The samples were incubated at room temperature for 25 minutes with gentle shaking. The magnetic particles were then separated by a magnetic separator obtained from Dynal, Inc. The supernatant from each vial was discarded and the magnetic particles were re-suspended in 1.5 milliliters of PBS. 300 microliters of the fluorescent magnetic particle suspension was used for each fluorescence measurement. A "Fluorolog III Spectrofluorometer", which was obtained from SPEX Industries, Inc. of Edison, N.J., was used to measure the fluorescence of the sample using a right angle mode. An excitation wavelength of 470 nanometers and an emission wavelength of 560 nanometers were used for the fluorescent magnetic particles, while an excitation wavelength of 570 nanometers and an emission wavelength of 605 nanometers were used for the fluorescent, non-magnetic particles. The integration time ranged from 0.2 to 1 second.

Figure 9:
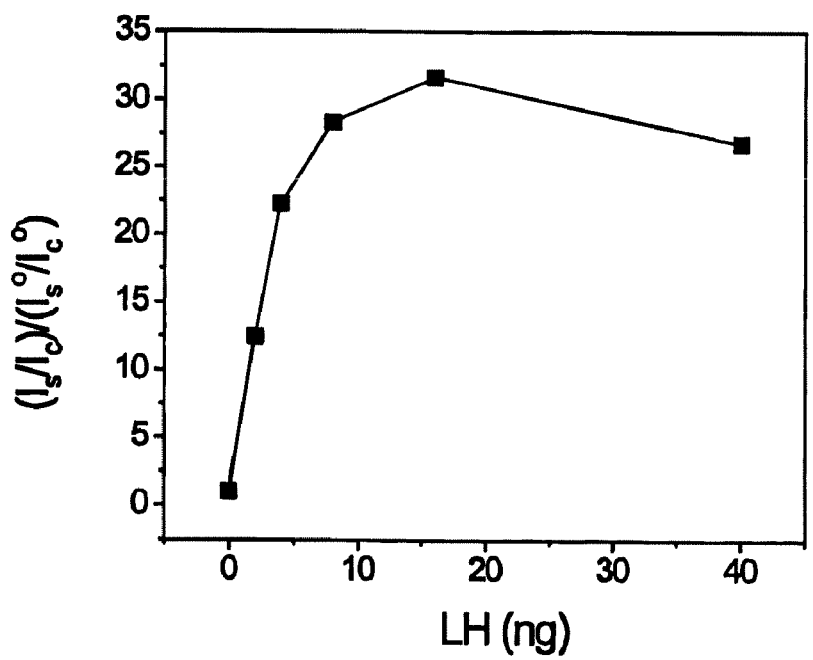
FIG. 9 shows the normalized fluorescent intensity versus the amount of leutinizing harmone (LH) as discussed in Example 2.

The normalized and calibrated fluorescence intensity as a function of the dose of LH in each sample is shown in FIG. 9.

The particles used in Example 2 were formed as follows:

Fluorescent Non-Magnetic Particles

The "fluorescent non-magnetic" particles were formed as described above in Example 1.

Fluorescent Magnetic Particles 2.76 milligrams of fluorescent superparamagnetic particles (2.5% solids in an aqueous suspension) were obtained from Polysciences, Inc. of Warrington, Pa. The particles were washed three times with borate buffers and separated by a magnetic separator obtained from Dynal, Inc. The washed particles were re-suspended in a 200-microliter borate buffer, and 82 micrograms of β-leutinizing hormone (β-LH) monoclonal antibody (1 milligram per milliliter, obtained from Fitzgerald Industries International, Inc.) were added. The mixture was gently mixed overnight at room temperature. The particles were then collected by a magnetic separator and incubated with 200 microliters of β-casein (10 milligrams per milliliter in borate buffer) for 30 minutes with gentle mixing to block the nonspecific binding sites. The blocked particles were washed twice with PBS and stored in 0.1 molar PBS.

Leutinizing Hormone (LH)

The "leutinizing hormone (LH)" was obtained from Fitzgerald Industries International, Inc.

EXAMPLE 3

A self-calibrated magnetic binding assay was compared to a non-calibrated magnetic binding assay.

Without Self-Calibration

Initially, the following components were added to 5 Eppendorf vials (Vial Nos. 2-6 in Table I):
(1) 15 microliters of covalently conjugated, non-fluorescent magnetic particles (3 milligrams per milliliter in 0.1 molar PBS buffer);
(2) 15 microliters of covalently conjugated, fluorescent non-magnetic particles (2 milligrams per milliliter in PBS buffer);
(3) 20 microliters leutinizing hormone (LH) analyte (1 microgram per milliliter); and
(4) 20 microliters of PBS.

A control Eppendorf vial was also formed with only 20 microliters of PBS (Vial No. 1 in Table I).

The samples were incubated at room temperature for 20 minutes with gentle shaking. The magnetic particles were then separated by a magnetic separator obtained from Dynal, Inc. The supernatant from each vial was discarded and the magnetic particles were re-suspended in 1.5 milliliters of PBS. 300 microliters of the fluorescent magnetic particle suspension was used for each fluorescence measurement. A "Fluorolog III Spectrofluorometer", which was obtained from SPEX Industries, Inc. of Edison, N.J., was used to measure the fluorescence of the sample using a right angle mode. An excitation wavelength of 570 nanometers and an emission wavelength of 605 nanometers were used for to take fluorescence measurements on different days.

Table I lists the relative fluorescence data for each day.

TABLE I

| | Fluorescent Measurements | | | | | | |
|---|---|---|---|---|---|---|---|
| | Vial | | | | | | Std. |
| | No. 1 | No. 2 | No. 3 | No. 4 | No. 5 | No. 6 | Dev % |
| Day 1 | 13 | 254 | 215 | 263 | 285 | 291 | 11 |
| Day 2 | 12 | 235 | 207 | 300 | 263 | 299 | 15 |
| Day 3 | 12 | 183 | 176 | 213 | 270 | 266 | 20 |
| Day 4 | 18 | 265 | 226 | 275 | 282 | 293 | 10 |
| Day 5 | 9 | 207 | 193 | 246 | 236 | 244 | 10 |
| Day 6 | 14 | 227 | 202 | 252 | 262 | 274 | 12 |
| Std. Dev % | 23 | 13 | 8 | 11 | 6 | 7 | |

With Self-Calibration

Initially, the following components were added to 5 Eppendorf vials (Vial Nos. 9-13 in Table II):
(1) 15 microliters of covalently conjugated, non-fluorescent magnetic particles (3 milligrams per milliliter in 0.1 molar PBS buffer);
(2) 15 microliters of covalently conjugated, fluorescent non-magnetic particles (2 milligrams per milliliter in PBS buffer);
(3) 20 microliters of fluorescent magnetic particles blocked by β-casein (3 milligrams per milliliter in PBS buffer); and
(4) 20 microliters leutinizing hormone (LH) analyte (1 microgram per milliliter); and
(5) 20 microliters of PBS.

A control Eppendorf vial was also formed with only 20 microliters of PBS (Vial No. 8 in Table II).

The samples were incubated at room temperature for 20 minutes with gentle shaking. The magnetic particles were then separated by a magnetic separator obtained from Dynal, Inc. The supernatant from each vial was discarded and the magnetic particles were re-suspended in 1.5 milliliters of PBS. 300 microliters of the fluorescent magnetic particle suspension was used for each fluorescence measurement. The "Fluorolog III Spectrofluorometer" was used to measure the fluorescence of the sample using a right angle mode. An excitation wavelength of 470 nanometers and an emission wavelength of 560 nanometers were used for the fluorescent magnetic particles, while an excitation wavelength of 570 nanometers and an emission wavelength of 605 nanometers were used for the fluorescent, non-magnetic particles. Table II lists the relative fluorescence data for each day.

TABLE II

| | Fluorescent Measurements | | | | | | |
|---|---|---|---|---|---|---|---|
| | Vial | | | | | | Std. |
| | No. 8 | No. 9 | No. 10 | No. 11 | No. 12 | No. 13 | Dev % |
| Day 1 | 31/32 | 352/47 | 344/43 | 300/41 | 318/44 | 369/39 | 12 |
| Day 2 | 31/42 | 324/42 | 329/41 | 323/46 | 338/47 | 418/43 | 14 |
| Day 3 | 28/39 | 307/40 | 333/42 | 282/42 | 288/40 | 425/46 | 12 |
| Day 4 | 30/41 | 267/36 | 292/36 | 271/41 | 281/38 | 356/43 | 8.8 |
| Day 5 | 21/29 | 252/33 | 292/34 | 258/38 | 275/36 | 328/37 | 10 |
| Day 6 | 21/25 | 237/33 | 307/38 | 265/40 | 288/35 | 358/39 | 12 |
| Std. Dev % | 13 | 3 | 3 | 4 | 5 | 6 | |

As can be seen from the comparisons of each set of samples for the two systems, the standard deviations (Std. Dev %) for the self-calibrated system were significantly smaller than the standard deviations without self-calibration, even under carefully controlled conditions. Because the self-calibrated system is less dependent on the measurement conditions, it is anticipated that the standard deviations for the self-calibrated system would be even smaller than the standard deviations without self-calibration when the conditions are not carefully controlled.

The particles used in Example 3 were formed as follows:

Non-Fluorescent Magnetic Particles

The "non-fluorescent magnetic" particles were formed as described above in Example 1.

Fluorescent Non-Magnetic Particles

The "fluorescent non-magnetic" particles were formed as described above in Example 1.

Fluorescent Magnetic Particles

The "fluorescent magnetic particles" were formed as described in Example 2.

Leutinizing Hormone (LH)

The "leutinizing hormone (LH)" was obtained from Fitzgerald Industries International, Inc.

EXAMPLE 4

The ability to detect the presence of an analyte using a sandwich assay, such as shown in FIG. 3, was demonstrated. Initially, the following components were added to six Eppendorf vials:
(1) 30 microliters of covalently conjugated, non-fluorescent magnetic particles (2 milligrams per milliliter in PBS buffer);
(2) 20 microliters of covalently conjugated, fluorescent non-magnetic particles (2 milligrams per milliliter in PBS buffer);
(3) 15 microliters of fluorescent magnetic particles blocked by β-casein (1 milligram per milliliter in PBS buffer); and
(4) C-reactive protein (CRP) analyte ranging from 0, 5, 10, 20, 50, and 100 microliters (0.2 micrograms per milliliter in PBS).

Figure 10:
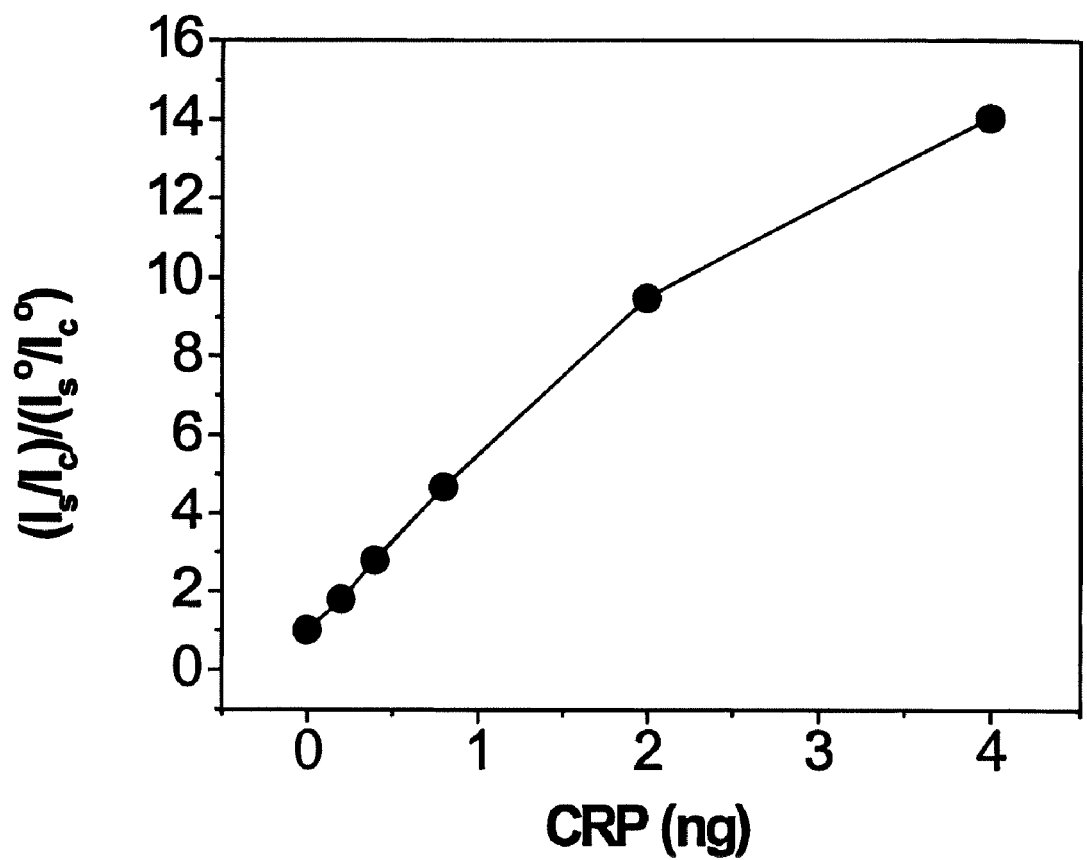
FIG. 10 shows the normalized fluorescent intensity versus the amount of C-reactive protein (CRP) as discussed in Example 4.

The samples were incubated at room temperature for 20 minutes with gentle shaking. The magnetic particles were then separated by a magnetic separator obtained from Dynal, Inc. The supernatant from each vial was discarded and the magnetic particles were re-suspended in 1.5 milliliter of PBS. 300 microliters of the fluorescent magnetic particle suspension was used for each fluorescence measurement. A "Fluorolog III Spectrofluorometer", which was obtained from SPEX Industries, Inc. of Edison, N.J., was used to measure the fluorescence of the sample using a right angle mode. An excitation wavelength of 470 nanometers and an emission wavelength of 560 nanometers were used for the fluorescent magnetic particles, while an excitation wavelength of 570 nanometers and an emission wavelength of 605 nanometers were used for the fluorescent, non-magnetic particles. The integration time ranged from 0.2 to 1 second. The normalized fluorescence intensity as a function of the dose of CRP in each sample is shown in FIG. 10.

The particles used in Example 4 were formed as follows:

Non-Fluorescent Magnetic Particles 125 microliters of 10% carboxylate-modified paramagnetic particles (0.35 microns, Estapor® Superparamagnetic microspheres, available from Bang's Laboratories, Inc.) were washed once by 1.5 ml carbonate buffer and twice by phosphate buffer saline (PBS) using a magnetic separator. The washed particles were re-suspended in 0.6 milliliters PBS and 15 milligrams carbodiimide (from Polysciences, Inc.). The mixture was allowed to react at room temperature (RT) for 30 minutes on a shaker. The activated particles were then washed twice with a borate buffer. The activated particles were again re-suspended in 1.2 ml borate buffer. Thereafter, 30 microliters of anti-C-reactive protein (anti-CRP1) monoclonal antibody (Mab A5804, 2 mg/ml, obtained from BiosPacific, Inc.) were added to the activated particles. The reaction mixture was allowed to react at room temperature on a shaker overnight. The activated particles were then collected and incubated in 1 milliliter of 0.1 molar ethanolamine under gentle shaking for 15 minutes. The particles were then washed twice with PBS and stored at 4° C. in a buffer that contained 0.1 molar PBS, 0.15 molar NaCl, 1% β-casein, 5% glycerol and 0.1% $NaN_3$.

Fluorescent Non-Magnetic Particles

The "fluorescent non-magnetic" particles were covalently conjugated according to the procedure described above, except that the binding member was anti-C-reactive protein (anti-CRP2) monoclonal antibody (2 mg/ml, obtained from BiosPacific, Inc.) instead of anti-CRP1. The particles utilized were FluoSpheres® carboxylate-modified microspheres, which were obtained from Molecular Probes, Inc. The particles had a particle size of 0.5 μm, and were red fluorescent with an excitation wavelength of 580 nanometers and an emission wavelength of 605 nanometers.

Fluorescent Magnetic Particles 100 microliters of a 2.76% solids suspension of fluorescent superparamagnetic particles (obtained from Polysciences, Inc. of Warrington, Pa.). Such particles have a mean diameter between 1 to 2 microns, and are believed to be iron-containing microspheres that have a polystyrene surface that allows for passive adsorption and functional group reactions with proteins. 1 milliliter of a borate buffer (0.1 molar, pH=8.5) was then added to the particles in an Eppendorf tube. The particles were separated by a magnetic separator obtained from Dynal, Inc. and the particles were re-suspended in 200 microliters of a 10 mg/ml solution of β-casein in a 0.1 M borate buffer. The suspension was incubated for 30 minutes with gentle mixing. The above step was repeated twice. The separated particles were re-suspended in 200 microliters of PBS and stored at 4° C.

C-Reactive Protein (CRP)

The "C-reactive protein (CRP)" was obtained BiosPacific, Inc.

EXAMPLE 5

The ability to form a membrane-based assay was demonstrated. Initially, Millipore SX porous membrane samples made of nitrocellulose were laminated onto corresponding supporting cards having a length of approximately 30 centimeters. A cellulosic fiber wicking pad (Millipore Co.) was attached to one end of the membrane. The other end of the membrane was laminated with two glass fiber pads (sample and conjugate pads). The conjugate pad and wicking pad were in direct contact with the membrane, and the sample pad was in direct contact with the conjugate pad.

The sample pad of each sample was then treated with 2% polyoxyethylene sorbitan monolaurate (a nonionic surfactant available from Sigma-Aldrich under the name "Tween 20") and dried at 37° C. for 1 hour. The conjugate pad was soaked with non-fluorescent magnetic particles, fluorescent non-magnetic particles, fluorescent magnetic particles, Tween 20 and sucrose, and then dried at 37° C. for 1 hour. The "non-fluorescent magnetic particles", "fluorescent non-magnetic particles", and "fluorescent magnetic particles" were formed as described above in Example 1.

A magnet strip was laid below the middle portion of each sample to form a detection zone. Thereafter, 40 microliters of PBS buffer was applied to the sampling pad of a first sample, 40 microliters of leutinizing hormone (LH) (0.5 micrograms/milliliter) was applied to the sampling pad of a second sample, and 40 microliters of LH (5 micrograms/milliliter) were applied to the sampling pad of a third sample. After 30 minutes, the fluorescent magnetic particles and fluorescent non-magnetic particles captured at the detection zone were measured with a "Fluorolog III Spectrofluorometer" using a front face mode and an angle of 30° relative to the sample. An excitation wavelength of 470 nanometers and an emission wavelength of 560 nanometers were used for the fluorescent magnetic particles, while an excitation wavelength of 560 nanometers and an emission wavelength of 605 nanometers were used for the fluorescent, non-magnetic particles.

The fluorescence detection signals for the above three samples were 187000, 217000 and 271000 counts, respectively. The fluorescence calibration signals for the above three samples were 99000, 103000 and 81000 counts, respectively.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method for detecting the presence or quantity of an analyte residing in a test sample, said method comprising:
   i) providing a membrane-based device, said device comprising a porous membrane that defines a detection zone and is in fluid communication with:
      detection probes that comprise non-magnetic particles conjugated with a first specific binding member and labeled with a detectable substance that is configured to emit a detection signal, the first specific binding member being capable of binding with the analyte;
      calibration probes that comprise magnetic particles labeled with a detectable substance that is configured to produce a calibration signal; and
      non-labeled magnetic particles conjugated with a second binding member, the second binding member also being capable of binding with the analyte;
   ii) contacting said detection probes, said calibration probes, and said non-labeled magnetic particles with the test sample so that complexes are formed between said detection probes, analyte, and non-labeled magnetic particles;
   iii) immobilizing said calibration probes and said complexes within said detection zone using a magnetic device;
   iv) exciting said detection probes and said calibration probes within said detection zone, wherein said excitation causes said detection probes to emit said detection signal and said calibration probes to emit said calibration signal;
   v) measuring the intensity of the detection signal at a first emission wavelength and the intensity of the calibration signal at a second emission wavelength; and
   vi) comparing the intensity of the detection signal to the calibration signal, wherein the amount of the analyte within the test sample is proportional to the intensity of the detection signal calibrated by the intensity of the calibration signal.

2. The method of claim 1, wherein the device further comprises a blocking agent configured for binding to the magnetic particles of the calibration probes.

3. The method of claim 1, wherein the device further comprises a conjugate pad in fluid communication with the porous membrane and positioned upstream from the detection zone, the conjugate pad comprising the detection probes and calibration probes.

4. The method of claim 1, wherein the detectable substance of both the detection probes and the calibration probes includes a luminescent compound.

5. The method of claim 1, wherein the detectable substance of both the detection probes and the calibration probes includes a fluorescent compound.

6. The method of claim 1, wherein the first specific binding member, the second specific binding member, or both include an antigen, hapten, aptamer, antibody, or a combination thereof.

7. The method of claim 1, wherein the magnetic particles of the calibration probes are conjugated with a third specific binding member.

8. The method of claim 1, wherein said first emission wavelength is different than said second emission wavelength.

9. The method of claim 1, wherein said detection probes and said calibration probes are excited separately.

10. The method of claim 1, wherein the intensity of said detection signal and said calibration signal are measured separately.

* * * * *